United States Patent
Yang et al.

(10) Patent No.: US 8,652,564 B2
(45) Date of Patent: Feb. 18, 2014

(54) AMINATED MATERIALS FOR ASSAYS

(75) Inventors: Shang-Tian Yang, Dublin, OH (US); Yunling Bai, Cockeysville, MD (US)

(73) Assignee: The Ohio State University Research Foundation, Columbus, OH (US)

(*) Notice: Subject to any disclaimer, the term of this patent is extended or adjusted under 35 U.S.C. 154(b) by 1705 days.

(21) Appl. No.: 11/745,283

(22) Filed: May 7, 2007

(65) Prior Publication Data

US 2007/0264676 A1 Nov. 15, 2007

Related U.S. Application Data

(60) Provisional application No. 60/798,470, filed on May 8, 2006.

(51) Int. Cl.
*B05D 3/00* (2006.01)

(52) U.S. Cl.
USPC .............................. 427/2.13; 436/518; 427/4

(58) Field of Classification Search
None
See application file for complete search history.

(56) References Cited

U.S. PATENT DOCUMENTS

| | | | |
|---|---|---|---|
| 5,583,213 A | 12/1996 | Yafuso et al. | |
| 6,090,995 A | 7/2000 | Reich et al. | |
| 6,303,179 B1 | 10/2001 | Koulik et al. | |
| 6,733,894 B2* | 5/2004 | Ho et al. | 506/16 |
| 2002/0112743 A1* | 8/2002 | Tabani et al. | 134/22.12 |
| 2004/0121339 A1* | 6/2004 | Zhou et al. | 435/6 |
| 2005/0009954 A1* | 1/2005 | Gebhard et al. | 523/210 |
| 2005/0214803 A1 | 9/2005 | Wang | |
| 2006/0094852 A1 | 5/2006 | Yuan et al. | |
| 2006/0160243 A1* | 7/2006 | Tang et al. | 436/177 |

OTHER PUBLICATIONS

Van Ness et al., A versatile solid support system for oligodeoxynucleotide probe-based hybridization assays, 1991, Nucleic Acids Res, 19(12): pp. 3345-3350.*
Fixe et al., Functionalization of poly(methyl methacrylate) (PMMA) as a substrate for DNA microarrays, 2004, Nuc Acid Res, 32(1e9), pp. 1-8.*
Bai, Yunling, "Surface Modifications for Enhanced Immobilization of Biomolecules: Applications in Biocatalysis and Immuno-Biosensor", Dissertation, 2006.
International Search Report dated Feb. 27, 2008.
Bai et al., "Surface Modification for Enhancing Antibody Binding on Polymer-Based Microfluidic Device for Enzyme-Linked Immunosorbent Assay", *Langmuir* 2006, 22, 9458-9467.
Lai et al., "Design of a Compact Disk-like Microfluidic Platform for Enzyme-Linked Immunosorbent Assay", *Anal. Chem.* 2004, 76, 1832-1837.
Henry et al., "Surface Modification of Poly(methyl methacrylate) Used in the Fabrication of Microanalytical Devices", *Anal. Chem.* 2000, 72, 5331-5337.
Fixe et al., "Functionalization of poly(methyl methacrylate) (PMMA) as a substrate for DNA Microarrays", *Nucleic Acids Research*, 2004, vol. 32, No. 1 e9 DOI: 10.1093/nar/gng 157.
Bulmus et al., "Modified PMMA monosize microbeads for glucose oxidase immobilization", *The Chemical Engineering Journal* 65 (1997) 71-76.

(Continued)

*Primary Examiner* — N. C. Yang
(74) *Attorney, Agent, or Firm* — Fay Sharpe LLP

(57) ABSTRACT

Protein binding onto a polymeric surface is enhanced by treating the surface with an amine-bearing polymer like poly (ethylene imine). When used in ELISA, the treated surface improves the performance of the assay.

18 Claims, 15 Drawing Sheets

(56) References Cited

OTHER PUBLICATIONS

Chen et al., "Controlling Antibody Orientation on Charged Self-Assembled Monolayers", *Langmuir* 2003, 19, 2859-2864.

Walker et al., "A Novel Asymmetric Clamping Cell for Measuring Streaming Potential of Flat Surfaces", *Langmuir* 2002, 18, 2193-2198.

Bai et al., "Enzyme-Linked Immunosorbent Assay of *Escherichia coli* O157:H7 in Surface Enhanced Poly(methyl methacrylate) Microchannels", Department of Chemical and Biomolecular Engineering, The Ohio State University, Submitted to *Biotechnology Progress* (May 2, 2006).

Mao et al, "Design and Characterization of Immobilized Enzymes in Microfluidic Systems", *Anal. Chem.* 2002, 74, 379-385.

\* cited by examiner

AMINATED MATERIALS FOR ASSAYS

CROSS REFERENCE TO RELATED APPLICATIONS

This application claims priority to U.S. Provisional Application Ser. No. 60/798,470, filed May 8, 2006, which is incorporated herein in its entirety by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. DMI0419585 awarded by the National Science Foundation.

BACKGROUND

The present disclosure relates generally to aminated materials for Enzyme-Linked Immunosorbent Assays (ELISAS) and processes, compositions and devices for improving the performance of such assays. Enzyme-Linked Immunosorbent Assay (ELISA) is a commonly used immunoassay. It has been widely used for detection and quantification of biological agents (mainly proteins and polypeptides) in the biotechnology industry, and is becoming increasingly important in clinical, food safety, and environmental applications. ELISA uses an enzymatic reaction to convert substrates into products having a detectable signal (e.g., fluorescence). Each enzyme in the conjugate can covert hundreds of substrates into products, thereby amplifying the detectable signal and enhancing the sensitivity of the assay.

The general principles and procedures used in ELISA are described here with reference to a 96-well microtiter plate. For example, the following procedures can be utilized:
 (a) The first antibody (specific for the antigen to be assayed) is added to an ELISA plate. The first antibody is allowed to adsorb to the solid substrate surface. The excess antibody is removed from the plate by washing after incubation.
 (b) The wells are filled with blocking solution. The blocking solution provides proteins, which adsorb to all protein-binding sites and prevent subsequent nonspecific binding of antibody to the plate.
 (c) The sample is added. If the sample contains the targeted antigen, it will bond to the adsorbed first antibody to form an antigen-antibody complex. After incubation, the plate is washed.
 (d) The conjugate solution is added. The conjugate (the second antibody) is an appropriate enzyme-labeled ligand (usually an antibody), which will bond to the antigen. The conjugate solution is discarded and the plate is washed after incubation.
 (e) The developing solution containing the substrate is added, which reacts with the enzyme in the conjugate. Each enzyme is able to convert hundreds of substrate into products to enhance the sensitivity of the assay. The products of the reaction emit fluorescence or change the color of the solution.

Conventional ELISA is typically carried out in 96-well microtiter plates. This involves a series of mixing, reaction, and washing steps, which not only are laborious but also often lead to large errors and inconsistent results. It usually takes several hours or longer to complete one assay because of the long incubation time required in each step. The long incubation time is a result of inefficient mass transport by molecular diffusion from the solution to the solid surface, although the immuno-reaction itself is a rapid process.

Microchip-based immunoassays have attracted attention for their potential advantages of having a high specific surface area, very low reagent consumption, and reduced assay time due to the device's microscale. Several microfluidic devices for immunoassays and enzyme assays have been developed and tested. For example, Lai and coworkers have demonstrated the feasibility of performing ELISA using a poly (methyl methacrylate) (PMMA) compact disk microfluidic platform as described in U.S. patent application Ser. No. 11/561,149, filed Nov. 17, 2006. However, because the microfluidic devices have a large surface-to-volume ratio, controlling their surface properties is a critical issue. In general, the sensitivity of the microfluidic device is dependent on the total activity of the antibodies or enzymes attached on the surface. How the surface interacts with antibodies and other biomolecules also affects the specificity of the immunoassay. Since the total surface area of a microfluidic device is fixed, it is important to attain a high immobilization activity yield during the immunoassay. The conventional passive adsorption of antibodies onto the surface is mainly driven by hydrophobic interactions, which often cause protein denaturation and reduce the protein's functional sites or activity by more than 90%. This problem increases when the microdevice has a large specific surface area. Developing an efficient surface modification method to enhance the binding efficiency and activity of the target protein is therefore important.

Polymers are low-cost alternative substrates materials for microfluidic devices, offering a wide range of physical and chemical properties that afford good processability for mass production and recyclability. However, efficient surface treatment methods for facilitating protein binding on the polymer surface are not well-developed. Several protein-polymer surface binding methods have been used in immunoassays, ranging from simple protein passive adsorption on polystyrene beads, adsorption via lipid layers grafted on poly(dimethylsiloxane) (PDMS), to adsorption via protein A bound to a PDMS surface. In developing fluorescence-based biosensors, PMMA has many advantages because it is transparent, has a low fluorescence background, and can be easily fabricated. However, direct adsorption of antibodies to the PMMA surface, without any surface modification, yields a low binding efficiency because the antibody binds poorly onto the untreated PMMA surface. Although various surface modification methods have been developed to introduce functional amine groups on the PMMA surface, they either consist of many steps and yield a low surface amine density, or involve unstable intermediates and environmentally unfriendly solvents in their preparation.

It would be desirable to provide a surface modification method which introduces functional amine groups onto a polymeric surface with few steps and yielding a high surface amine density.

BRIEF DESCRIPTION

Disclosed herein, in various exemplary embodiments, are processes for introducing functional amine groups onto a polymeric surface. When such surfaces are utilized in immunoassays, protein/enzyme biochips, biocatalysts, etc., the surfaces exhibit enhanced performance.

In embodiments, a method for aminating the surface of a polymeric substrate is provided, comprising:
 providing a polymeric substrate having a surface;

contacting the surface with an amine solution comprising an amine-bearing polymer, the polymer having a reactive nitrogen atom in either the backbone or a pendant group; and drying the surface to obtain the polymeric substrate with an aminated surface.

The amine solution may comprise from about 0.1% to about 10% (w/v) of the polymer. In more specific embodiments, the amine solution comprises from about 0.2% to about 1% (w/v) of the polymer. The amine solution may have a pH of from about 7 to about 14. In specific embodiments, the amine-bearing polymer is poly(ethylene imine) or poly(allylamine hydrochloride).

The contacting step may occur at a temperature of from about 20° C. to about 100° C. In specific embodiments, the contacting step may occur at a temperature of from about 25° C. to about 50° C. The contacting step may occur for a period of from about 5 minutes to 12 hours.

The method may further comprise the step of treating the surface of the substrate with a basic solution. The basic solution may comprise from about 0.1 to about 6 N of NaOH and/or have a pH of from about 8 to 14. The treating step may occur at a temperature of from about 20° C. to about 100° C. The treating step may occur for a period of from about 5 minutes to 12 hours.

The method may further comprise the step of functionalizing the surface with a crosslinker solution comprising glutaraldehyde. The crosslinker solution may comprise from about 0.1% to about 10% (w/v) of glutaraldehyde. The functionalizing step may occur at a temperature of from about 20° C. to about 100° C. The functionalizing step may occur for a period of from about 5 minutes to 12 hours.

In other embodiments, a method for improving the performance of an enzyme-linked immunosorbent assay is disclosed, comprising:

providing a polymeric substrate having a surface which has been aminated with an amine-bearing polymer, the polymer having a reactive nitrogen atom in either the backbone or a pendant group; and performing the enzyme-linked immunosorbent assay upon the aminated surface.

In specific embodiments, the amine-bearing polymer may be poly(ethylene imine) or poly(allylamine hydrochloride).

In other embodiments, the aminated surface may bind about 5 to about 20 times more active antibodies than a polymeric surface which has not been aminated. In specific embodiments, the aminated surface binds about 10 times more active antibodies than a polymeric surface which has not been aminated.

In other embodiments, the ELISA signal for the aminated surface may be about 10 to about 100 times greater than the signal of a polymeric surface which has not been aminated. In specific embodiments, the ELISA signal for the aminated surface may be about 45 times greater than the signal of a polymeric surface which has not been aminated.

In other embodiments, the signal-to-noise ratio for the aminated surface may be about 1.5 to about 10 times greater than that of a polymeric surface which has not been aminated. In specific embodiments, the signal-to-noise ratio for the aminated surface may be about 3 times greater than that of a polymeric surface which has not been aminated.

Also disclosed is a method of aminating the surface of a poly(methyl methacrylate) substrate, comprising:

providing a poly(methyl methacrylate) substrate having a surface;

contacting the surface with an amine solution comprising poly(ethylene imine) and having a pH of from about 9 to about 13;

functionalizing the surface with a crosslinker solution comprising glutaraldehyde; and drying the surface to obtain a substrate with an aminated surface.

In embodiments, the amine solution has a pH of from about 9 to about 11.5.

In embodiments, the surface may be contacted with the amine solution at room temperature for about 1 hour. In other embodiments, the surface may be functionalized with the crosslinker solution at room temperature for about 30 minutes.

Apparatuses comprising aminated surfaces are also disclosed, as are methods and assays using such aminated surfaces.

These and other non-limiting aspects and/or objects of the development are more particularly disclosed below.

BRIEF DESCRIPTION OF THE DRAWINGS

The following is a brief description of the drawings, which are presented for the purposes of illustrating the development disclosed herein and not for the purposes of limiting the same.

DETAILED DESCRIPTION

Figure 1:
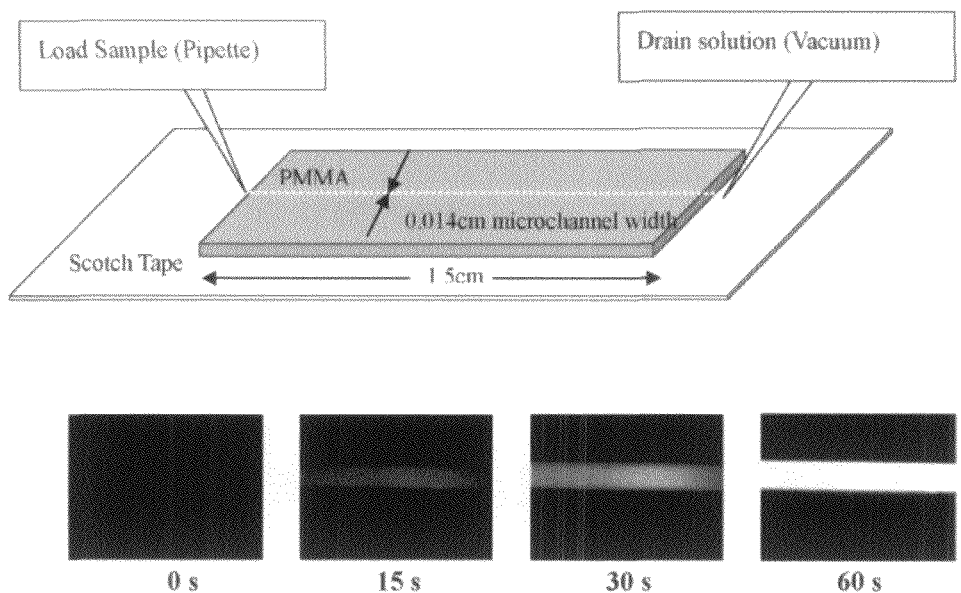
FIG. 1 is a diagram showing the configuration of a microchannel modified according to the processes of the instant disclosure.

A more complete understanding of the processes and apparatuses disclosed herein can be obtained by reference to the accompanying drawings. These Figures are merely schematic representations based on convenience and the ease of demonstrating the present development, and are, therefore, not intended to indicate relative size and dimensions of the imaging devices or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to component of like function.

The present disclosure describes processes for introducing functional amine groups onto a substrate surface. The processes comprise the steps of:

providing a polymeric substrate having a surface;

contacting the surface with an amine solution comprising an amine-bearing polymer, the polymer having a reactive nitrogen atom in either the backbone or a pendant group; and drying the surface to obtain the polymeric substrate with an aminated surface.

The substrate is generally a polymer. Suitable polymers include, but are not limited to, poly(methyl methacrylate) (PMMA), polyester, polyethylene terephthalate, polyurethane, and ester-containing polymers. Other suitable polymers include polymers with negative charges, such as polystyrene, polycarbonate, polyethylene, and polypropylene. In specific embodiments, the substrate is a PMMA substrate.

The amine solution comprises an amine-bearing polymer. The polymer has a reactive nitrogen atom in either the backbone or a pendant group. By "reactive," it is meant that the nitrogen atom is able to still react with another atom. In other words, the nitrogen atom has one or two hydrogen atoms covalently bonded to it; it is not a tertiary amine. In specific embodiments, the polymer is poly(ethylene imine) (PEI) or poly(allylamine hydrochloride) (PAH). Their monomeric and polymeric forms are shown below:

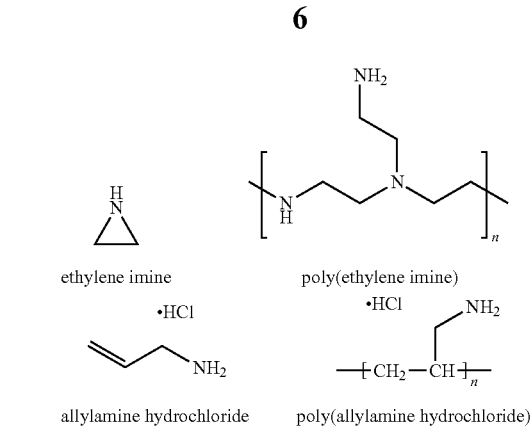

PEI has primary, secondary, and tertiary amines and is thus considered an amine-bearing polymer. The ratio of primary, secondary, and tertiary amines in PEI is 1:2:1. Only the primary and secondary amines are reactive.

The amine solution may comprise from about 0.1% to about 10% (w/v) of the polymer. The amine solution may have a pH of from about 7 to about 14. In particular embodiments, the pH is from about 7 to about 11.5 or from about 9 to about 13. The pH can be adjusted by choosing a particular solvent or by the addition of an acid or base. The amine solution further comprises a solvent in which the polymer is dissolved. The solvent is generally water.

The substrate is then contacted with the amine solution. Generally, the substrate is immersed in the amine solution. However, embodiments where the amine solution is deposited onto the substrate are also contemplated. The contacting step may occur at a temperature of from about 20° C. to about 100° C. (measured by the temperature of the amine solution). The contacting step may occur for a period of from about 5 minutes to 12 hours. In specific embodiments, the contacting step may occur for a period of from about 20 to about 60 minutes The pH of the amine solution may determine the amount of polymer that attaches to the substrate and how the polymer attaches to the substrate. At pH values less than about 9, PEI molecules are mainly electrostatically bound to the substrate surface. However, at pH values greater than about 9, PEI molecules are mainly covalently bound to the substrate surface. More PEI molecules can be bound to the substrate at pH higher than about 11 because covalently bound PEI molecules will not be washed away. In addition, PEI molecules (which are positively charged) may be bound to the surface of negatively charged polymers by electrostatic attraction.

The aminated surface is then dried, typically by air-blowing.

The substrate may be treated with a basic solution prior to applying the amine solution. The basic solution comprises NaOH in the range of from about 0.1 N to about 6N. The solvent is generally water. The basic solution can have a pH of from about 8 to 14 or in specific embodiments, from about 10 to 14. Again, the substrate can be treated by immersion or deposition of the basic solution. The contacting step may occur at a temperature of from about 20° C. to about 100° C. (measured by the temperature of the basic solution). The contacting step may occur for a period of from about 5 minutes to 12 hours.

After the substrate surface has been aminated, the surface may be further functionalized by the application of a crosslinker solution. The crosslinker solution comprises an aldehyde molecule having multiple functional aldehyde groups, the aldehyde molecule being present in the amount of from about 0.1% to about 10% (w/v). In specific embodiments, the aldehyde molecule is glutaraldehyde. By "functional," it is meant that the aldehyde group is able to still react with another atom. Again, the substrate can be treated by immersion or deposition of the crosslinker solution. The functionalizing step may occur at a temperature of from about 20° C. to about 100° C. (measured by the temperature of the crosslinker solution). The functionalizing step may occur for a period of from about 5 minutes to 12 hours.

If the additional solutions are used, then the surface may be rinsed with distilled water between each step.

In some specific embodiments, the substrate is treated with a basic solution and then contacted with the amine solution, wherein the amine solution has a pH of about 7. In alternately specific embodiments, the substrate is not treated with a basic solution at all, but is instead simply contacted with the amine solution, wherein the amine solution has a pH of about 11.

ELISA results are enhanced by the aminated surface created from the instant processes. A microchannel surface treated by the instant processes can bind about 5 to 20 times more active antibodies than a microchannel surface not treated by the instant processes. The signal may be 10 to 100 times higher and the signal to noise ratio may be 1.5 to 10 times higher as well. (Such comparisons are made using substrates of the same material, of course.) This makes microfluidic devices more sensitive and reliable.

The following examples are provided to illustrate the methods and apparatuses of the present disclosure. The examples are merely illustrative and are not intended to limit devices made in accordance with the disclosure to the materials, conditions, or process parameters set forth therein. All parts are percentages by weight unless otherwise indicated.

EXAMPLES

Example 1

Fabrication of PMMA Microchannel

A PMMA mold for microchannels (140 µm wide, 125 µm deep, and 1.5 cm long) was fabricated using a computer numerical controlled (CNC) machine. Polydimethylsiloxane (PDMS) was prepared from Sylgard 184 silicon elastomer base and curing agent (Dow Corning corporation, Midland, Mich.) at a 10:1 (w/w) ratio. After thorough mixing and degassing under vacuum for 30 min, the PDMS polymer was cast over the PMMA mold and cured in an oven at 70° C. for 1.5 to 2 hours. The PDMS daughter mold was then used to produce PMMA microchannels through a microembossing process. A schematic of the microfluidic ELISA device is shown in FIG. 1 along with fluorescence images of the microchannel at different times after the initiation of the enzyme reaction in ELISA.

Modification of PMMA Microchannels

To functionalize the PMMA surface, the microchannels were treated with four different amine-bearing chemicals:
1. poly(ethylene imine) (PEI): MW 75,000;
2. poly(allylamine hydrochloride) (PAH): MW 70,000;
3. hexamethylene diamine (HMD); and
4. 1,3-diaminopropane (DAP).

All were purchased from Sigma-Aldrich (St. Louis, Mo.).

For HMD or DAP treatment, the PMMA plates were incubated with 10% HMD or DAP in 100 mM, pH 11.5 borate buffer for 2 hours.

For PEI or PAH treatment, PMMA plates were first treated in 1 N NaOH solution at 55° C. for 30 min and then immersed in a PEI or PAH solution (0.2%, pH 7) at room temperature (25° C.) for 1 hour. The aminated PMMA plates were then placed in the glutaraldehyde solution (1% w/v) at room temperature (25° C.) for 30 min. The PMMA surface was thoroughly rinsed with distilled water after each treatment step.

After air-blow drying, the treated microchannels were ready for antibody binding.

ELISA for IgG Detection

In the ELISA, the rat IgG was the 'analyte' or antigen, the polyclonal affinipure goat anti-rat IgG (H+L) was the first antibody, and horseradish peroxidase-conjugated affinipure goat anti-rat IgG (H+L) was the second antibody. They were purchased from Jackson Immuno Laboratories, Inc. (West Grove, Pa.), reconstituted in distilled water and stored at −80° C. until use. The substrate solution was prepared by dissolving 3 g/L of 3-p-hydroxyphenylpropionic acid (HPPA) (Sigma-Aldrich, St. Louis, Mo.) in Tris-HCl buffer (0.15 M, pH 8.5). Prior to use, 1 µL of 30% hydrogen peroxide was added to every 7.5 mL of HPPA solution and mixed thoroughly. PBW washing buffer was prepared from Dulbecco's phosphate buffered saline, pH 7 (PBS) (Invitrogen Life Technologies, Carlsbad, Calif.) and contained 0.1% polyoxyethylenesorbitan monolaurate (Tween-20™; Bio-Rad Laboratories, Hercules, Calif.) and 0.5% bovine serum albumin (BSA) (Invitrogen Corporation, Grand Island, N.Y.). The blocking buffer contained PBS, 0.1% Tween-20™, 1% BSA, and 0.05% sodium azide (Sigma-Aldrich, St. Louis, Mo.).

ELISA procedures were carried out in modified PMMA microchannels, in pristine (untreated or passive adsorption) PMMA microchannels, and, for comparison purposes, in 96-well plates (Nunc Maxisorp).

Elisa in 96-Well Plate

To each well, 100 µL each of the following solution was added in sequence: first antibody (10 mg/L), blocking, antigen (0-10 mg/L), second antibody (10 mg/L), and substrate solutions. Between additions of the different solutions, the individual wells were washed with 200 µL of the washing solution three times. The first antibody was incubated in the well at 4° C. overnight. The other incubation steps were done at room temperature for 3 hours or at 4° C. overnight. The reaction was detected by a CytoFluor 96-well plate fluorescence reader using 360±40/460±40 nm as the excitation and emission filters, respectively.

ELISA in Microchannels

The microchannel was first sealed with the Scotch tape (see FIG. 1A). Unless otherwise noted, first antibody (10 mg/L), blocking, antigen (1 mg/L), and second antibody (10 mg/L) solutions, 1 µL each, were loaded, using a micropipette, into the microchannel from the opening at the side of the microchip in sequence to cover the whole channel area. Incubation was done in a humidified box at room temperature for 1 hour. The microchannel was thoroughly washed with 10 µL of PBW solution for three times between each step. The Scotch tape was replaced with new tape prior to the blocking and detection steps to eliminate the undesired binding of antibodies, antigen and substrate on the Scotch tape. Detection was carried out using an inverted fluorescence microscope (Nikon Eclipse TE2000-U). A 100-W mercury light source with a 335/20 nm filter and a dichroic mirror was used as the excitation source. The fluorescence emission signal was obtained through a dichroic mirror and a 405/40 nm filter. Following the reaction, the fluorescent microchannel images (see FIG. 1) were recorded with a 12-bit high-resolution monochrome digital camera system (CoolSnap HQ). The fluorescence intensity was analyzed using the Fryer Metamorph Image Analysis System. The average intensity of independent measurements from at least two different microchannels was used.

Surface Modification

Various amounts of the first antibody ranging from 0.1 to 10 mg/L were applied to the pristine, PEI modified, and HMD modified PMMA microchannels. After 1 hour incubation, the microchannels were washed and air-blow dried. The actual amounts of the first antibody bound to the microchannels were determined indirectly by completing the remaining ELISA steps. The enzyme reaction rate (RFU/sec) was monitored and used as an indicator of the enzyme activity, which was proportional to the amount of the first antibody bound on the microchannel surface when excessive amounts of antigen (1 mg/L) and second antibody (10 mg/L) were applied in the assay.

1 µL of streptavidin solution (10 mg/L) was added to the pristine (passive adsorption), PEI modified, and HMD modified PMMA microchannels. After 1 h incubation, these microchannels were washed with 10 µL of PBW solution for three times, followed by the addition of biotin-HRP solution (20 mg/L). The time response of the enzymatic reaction of HPPA was monitored and reported in RFU/sec, indicating the reaction rate or the enzyme activity, which is proportional to the amount of biotin or streptavidin bound to the surface. In order to study and compare the signal/noise ratio of different chemically modified surfaces, more concentrated streptavidin and biotin-HRP solutions, 200 mg/L, were utilized to increase the background noise to a non-zero level.

Surface Blocking

PEI treated microchannels were treated with various blocking reagents: no blocking, 1% ethanolamine, 1% polyethylene glycol-$NH_2$ (PEG-$NH_2$), 1% bovine serum albumin (BSA), 1% ethanolamine+1% BSA, and 1% PEG-$NH_2$+1% BSA. This experiment evaluated their effectiveness at blocking or preventing non-specific protein binding. After blocking, 20 mg/L of the second antibody was applied to the microchannels, followed with washing and the enzyme reaction. The enzyme reaction was monitored and RFU/sec was used to indirectly assess the amount of second antibody non-specifically bound to the surface, indicating the effectiveness of these different blocking conditions.

Adsorption/Binding Rate and Kinetics

The protein adsorption kinetics was studied by loading 1 µL of the first antibody solution (1 mg/L) into each microchannel, which was then placed with face down in a Petri dish whose surface had been pre-treated with the blocking solution for 1 hour. The microchannels were incubated at room temperature (25° C.) for various periods of time. After incubation, the microchannels were washed, air-blow dried, sealed with Scotch tape, and then followed by the blocking and other remaining ELISA steps. The binding kinetics between the antigen and the first antibody on the microchannel surface was also studied. Each microchannel was loaded with 1 µL of the first antibody solution (10 mg/L) and incubated for 1 h, washed, air-blow dried, sealed with Scotch tape, blocked with the blocking solution for 1 h. After blocking, 1 µL of the antigen solution (1 mg/L) was added into each microchannel and incubated for various time periods, followed by completing the remaining ELISA steps.

X-ray Photoelectron Spectroscopy (XPS)

The surface elementary compositions of the PMMA plates before and after amination with HMD or PEI were analyzed with a Krotos AXIS ultra X-ray photoelectron spectrometer. Measurements were obtained using a monochromatic Al Kα X-ray source (240 W) and charge neutralization. The samples were analyzed with a 900 take-off angle. Deconvolution of spectral peaks was performed using the Kratos software and the spectra of C(1s) (280-300 eV binding energy), O(1 s) (528-542 eV binding energy), and N(1s) (392-410 eV binding energy) were recorded.

Atomic Force Microscopy (AFM)

A 2.5% (w/w) PMMA/toluene solution was prepared by dissolving the PMMA pellets in toluene, which was filtered through a 0.2-µm membrane filter. The PMMA solution was then spin coated onto a clean silicon wafer at 1500 rpm for 30 seconds and the PMMA-coated silicon wafer was annealed at 150° C. in a vacuum oven for 24 hours. After annealing, the PMMA surfaces were treated with PEI or HMD, followed by antibody binding. All the solutions were prepared with 18 MΩ·cm water. The surface morphology of the modified and protein bound PMMA thin film was investigated in air, using a Nanoscope Ø AFM (Digital Instruments, Santa Barbara, Calif.) in the tapping mode, with a low spring constant of 0.3 N/m, and at ambient temperature.

Results

Modification of PMMA Microchannels

Figure 2:
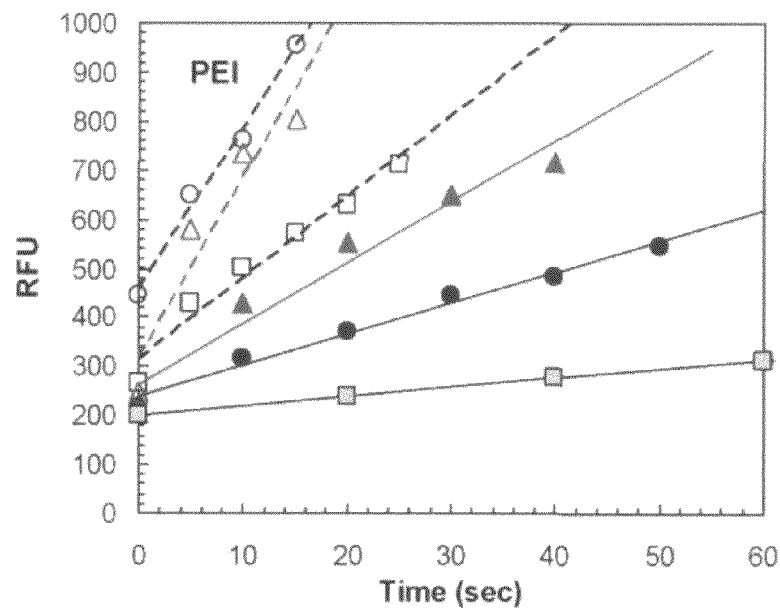
FIG. 2 is a graph showing the time course of an enzymatic reaction in a PEI-treated PMMA microchannel.
Figure 3:
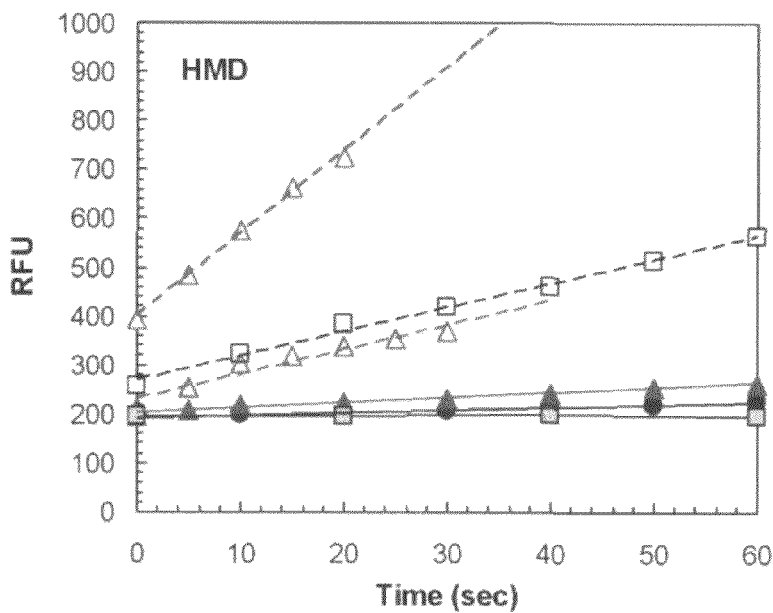
FIG. 3 is a graph showing the time course of an enzymatic reaction in a HMD-treated PMMA microchannel.
Figure 4:
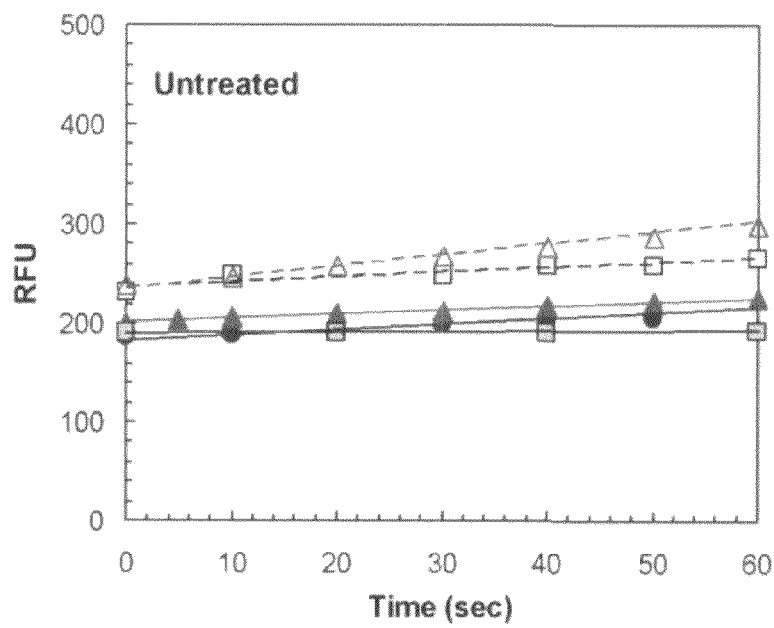
FIG. 4 is a graph showing the time course of an enzymatic reaction in an untreated PMMA microchannel.

FIGS. 2-4 show the time courses of the enzymatic reaction of HPPA as monitored by the fluorescence intensity (RFU) for the PMMA microchannels with PEI, HMD, or pristine surfaces. Various initial first antibody concentrations were used: 0 mg/L (filled square); 0.1 mg/L (filled circle); 0.5 mg/L (filled triangle); 1 mg/L (open square); 5 mg/L (open circle); and 10 mg/L (open triangle). FIG. 2 is the PEI-treated PMMA microchannel. FIG. 3 is the HMD-treated PMMA microchannel. FIG. 4 is the untreated PMMA microchannel.

The enzyme reaction generally was faster when more first antibodies were bound to the microchannel surface in the ELISA, suggesting that more antigens and thus second antibody-enzyme conjugates could bind to the surface when there were more active first antibodies. The slope of the time-course plot indicates the initial reaction rate, which should be proportional to the enzyme activity, and thus can be used as an indirect assessment of the amount of active first antibody available on the microchannel surface for the immuno reaction.

Figure 5:
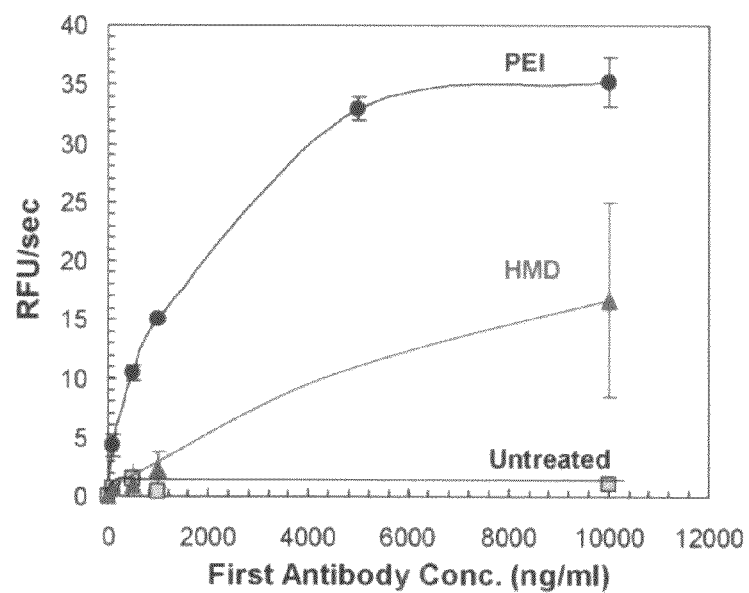
FIG. 5 is a graph showing the effect of the first antibody concentration on the reaction rate on various modified surfaces.

The effects of the first antibody concentration and different surface treatments on the reaction rate, expressed as RFU/sec, are shown in FIG. 5. The first antibody concentration ranged from 0.1 mg/L to 10 mg/L. It is noted that the level of RFU/sec should be proportional to the actual amount of active first antibody bound to the surface when there are excessive amounts of antigen and second antibody. The reaction rate generally increased with increasing first antibody concentration applied in the experiments, but leveled off at higher concentrations. However, for different surfaces, the reaction rates were very different even though the same amount of the first antibody was applied, indicating that the binding efficiency for the first antibody on these different surfaces was quite different. The pristine surface yielded the least active antibody at all initial first antibody concentrations studied. For the HMD modified PMMA surface, the fluorescence signal was comparable to that of the pristine surface at low first antibody concentrations, but increased substantially as the first antibody concentration increased to 10 mg/L. For the PEI modified PMMA surface, the fluorescence signal was the highest at all initial first antibody concentrations studied. It was about 10 times higher at 1 mg/L of the first antibody concentration as compared to those from the HMD modified and pristine surfaces. Also, the data from the PEI modified surfaces were more consistent with smaller standard errors than those from the HMD modified surface. It is clear that PEI treatment resulted in the highest binding efficiency for the first antibody. It is also clear that the ELISA performance is strongly dependent on the amount of the first antibody bound on the surface, which greatly affects the subsequent antigen-antibody binding and final enzyme reaction rate. Therefore, proper surface treatment to increase the binding efficiency of the first antibody on the PMMA microchannel surface is critically important to the microfluidic ELISA.

Surface Modification

Figure 6:
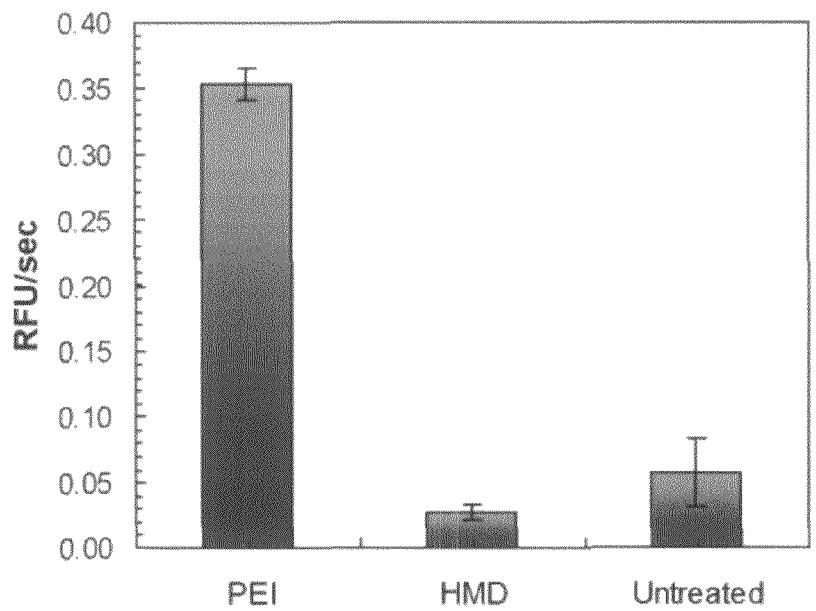
FIG. 6 is a graph showing the effects of different surface treatment methods on streptavidin binding.
Figure 7:
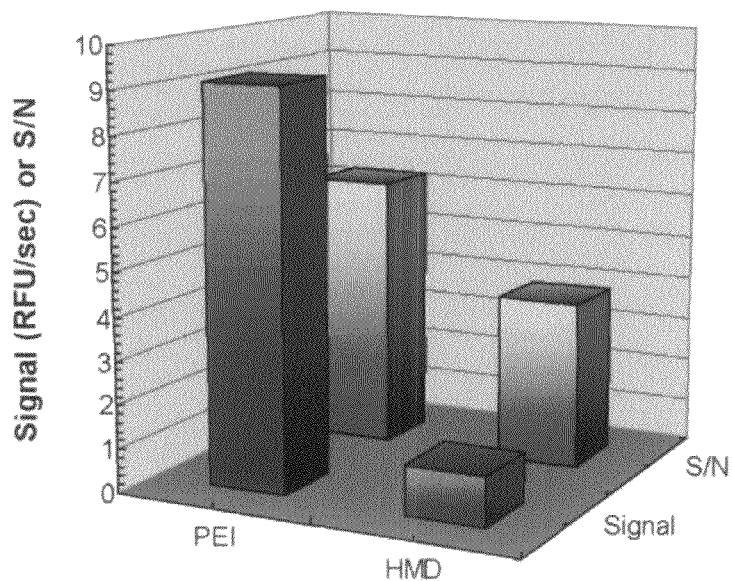
FIG. 7 compares the signal and signal-to-noise ratio of two surfaces that have been treated with streptavidin.

FIGS. 6 and 7 show the effects of the different surface treatment methods on streptavidin binding. FIG. 6 shows the signal given from each modified surface. Here, 10 mg/L of streptavidin and 20 mg/L of biotin-HRP were used. Compared to the HMD modified and pristine surfaces, the PEI treated surface gave ~10 times higher signal regardless of the level of the background noise, which was zero when the concentrations of streptavidin and biotin-HRP were low but increased significantly with increasing concentrations in the assay. FIG. 7 compares the signal and signal-to-noise ratio (S/N ratio) of the PEI-treated and HMD-treated surfaces. Here, 200 mg/L of streptavidin and 200 mg/L of biotin-HRP were used. The S/N ratio from the PEI treated microchannel was ~2 times that from the HMD treated microchannel. It is thus clear that the PEI treated surface can give the highest fluorescence signal at a faster rate and a better S/N ratio. Both are critical to ELISA's sensitivity and detection limit.

Figure 8:
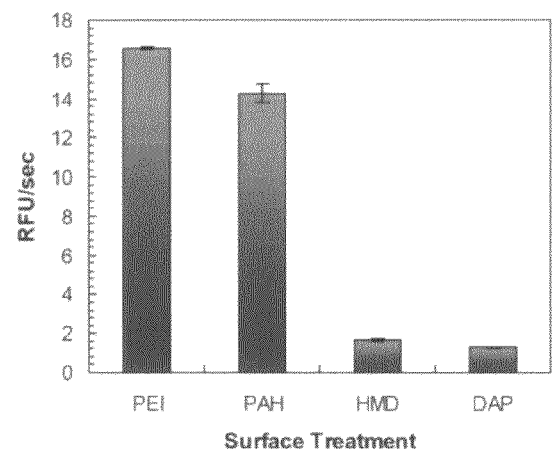
FIG. 8 is a graph showing the spacer effect of four different amine molecules on the reaction rate.

The interaction between the first antibody and the different PMMA surfaces can be attributed to the spacer effect. FIG. 8 shows the effect of the different amine molecules PEI, PAH, HMD, and DAP on the enzyme reaction rate. In these experiments, 1 mg/L first antibody, 1 mg/L antigen, and 10 mg/L second antibody were used. The PMMA surfaces treated with the two polymers bound ~10 times more active antibodies than those treated with the two small diamine molecules. Clearly, the two amine-bearing polymers were better than the small diamine molecules for antibody binding because the spacer function of polymers can preserve most of the biological activity of the bound protein molecules. The spacer effect allowed the proteins of the antibody to stay away from the PMMA surface, thus preserving more activity than those bound closer to the surface.

Surface Blocking

Figure 9:
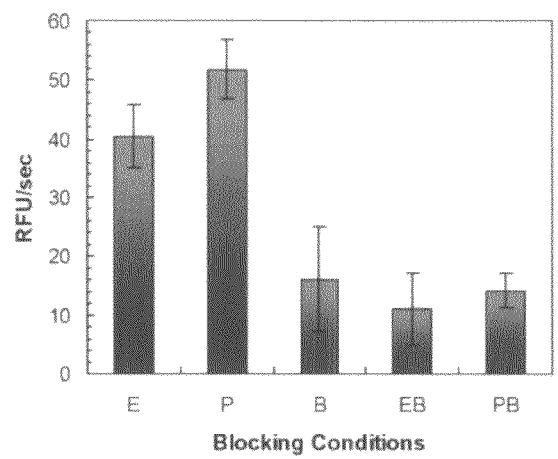
FIG. 9 is a graph comparing the effect of different blocking agents on the reaction rate.

FIG. 9 shows the results of the surface blocking experiments. PEI treatment greatly increased the binding efficiency of the first antibody on the PMMA surface. However, it also would greatly increase non-specific binding of antigen and second antibody if the surface were not properly blocked. Therefore, it was necessary to evaluate and optimize the blocking conditions for the PEI-treated PMMA surface. Different blocking agents were studied for their effectiveness in preventing non-specific protein adsorption. In FIG. 9, the following abbreviations were used: E for 1% ethanolamine; P for 1% PEG-NH$_2$; B for 1% BSA; EB for 1% ethanolamine+1% BSA; and PB for 1% PEG-NH$_2$+1% BSA. 10 mg/L of the second antibody was added to test the blocking effectiveness. Since first antibody and antigen were not added to the microchannels in the experiment, any enzyme reaction observed was attributable to the second antibody-enzyme conjugates directly bound on the surface. Ethanolamine and PEG-NH$_2$ were not effective in blocking the surface, whereas BSA at 1% was an efficient blocking agent. Adding ethanolamine or PEG-NH$_2$ to BSA solution did not improve the blocking.

Adsorption/Binding Rate and Kinetics

Figure 10:
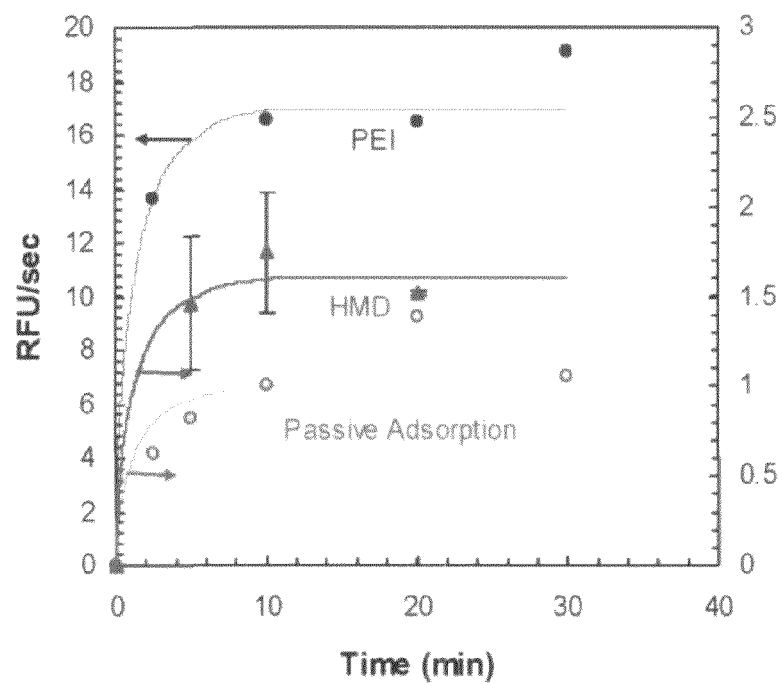
FIG. 10 is a graph showing the first antibody binding kinetics on various modified surfaces.
Figure 11:
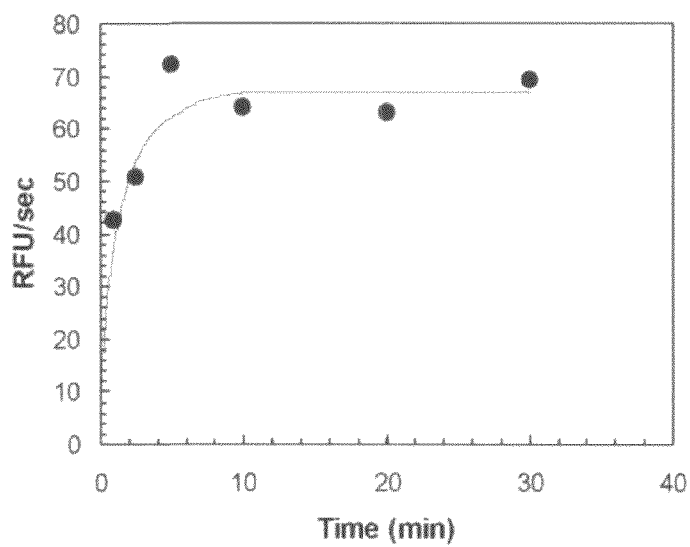
FIG. 11 is a graph showing the antigen binding kinetics on first antibody bound PEI-treated PMMA.

FIGS. 10 and 11 show the results of the protein adsorption/kinetics experiments. The rate at which the antibody binds to the PMMA surface will determine the incubation time for each ELISA step and the total assay time required to complete each assay. FIG. 10 is a graph showing the first antibody binding kinetics on various modified surfaces (pristine, HMD, PEI). 1 mg/L first antibody, 1 mg/L antigen, and 10 mg/L second antibody were used. Generally, the fluorescence signal increased rapidly at the beginning and then reached a plateau when all antibodies had been adsorbed to the surface. The time to reach the plateau was the same (~10 minutes) for all three different surfaces studied, although the PEI-treated surface gave much higher signals than those from the HMD treated and untreated surfaces. The results suggest that the adsorption of antibody on different surfaces was controlled by the same mechanism: diffusion, which has been reported as the rate limiting step in the heterogeneous immunosorption reaction on the planar surface and microchannels. The binding kinetics were not affected by the reagent loading as the time to load (pipette and fill) the entire microchannel was less than 1 second. Therefore, any possible effects of convection and mixing on antibody adsorption onto the microchannel surface can be neglected.

The adsorption kinetics of antibody can be modeled by Fick's second law:

$$\frac{\partial C}{\partial t} = D\left(\frac{\partial^2 C}{\partial x^2} + \frac{\partial^2 C}{\partial y^2}\right) \quad (1)$$

where C stands for the concentration of the first antibody in the solution; and x and y are the width and depth of the microchannel, respectively. D is the diffusion coefficient, which can be estimated using the semi-empirical equation of Polson:

$$D_{AB} = \frac{9.40 \times 10^{-15} \, T}{\mu(M_A)^{1/3}} \quad (2)$$

The antibody studied had a molecular weight of 160,000 kg/kg mol, and therefore, D was calculated to be $5.14 \times 10^{-7}$ cm$^2$/sec. Because the length of the microchannel was much longer than the cross sectional dimension, the model only considered two dimensions. The initial condition and boundary conditions were as follows:

At t=0, C=C$_0$

At t>0, C=0 at the three microchannel walls: (x=0, x=140 μm, and y=0)

$\partial C/\partial y=0$ at the surface in contact with the blocked wall of the Petri dish (y=125 μm)

C=0 at the microchannel wall could be assumed since the binding reaction of the antibody on the polymer surface was much faster than its diffusion to the wall. The open channel side could be treated as an insulated surface since it was in contact with the blocked surface of the Petri dish.

Equation (1) was used to calculate the antibody concentration in the solution and the amount of antibody adsorbed on the surface of the microchannel (dimensions: 140 μm×125 μm) at any time point. The calculated results were then adjusted with a proportional constant to fit the plateau value shown in FIG. 10. In general, the model simulates the data well, confirming that the adsorption of the first antibody in the microchannel was controlled by diffusion.

The binding kinetics for the antigen, rat IgG, which also has a molecular weight of 160,000 kg/kg mol, in the microchannel was also studied and simulated using the same mathematical model and diffusion coefficient ($5.14 \times 10^{-7}$ cm$^2$/sec), and the results are shown in FIG. 11. Here, 10 mg/L first antibody, 1 mg/L antigen, and 10 mg/L second antibody were used. Again, the model simulation is in good agreement with the experimental data. This result suggests that the reaction between the antigen and antibody is much faster than the diffusion, which is consistent with previous studies.

ELISA in Microchannels Vs. 96-Well Plate

Figure 12:
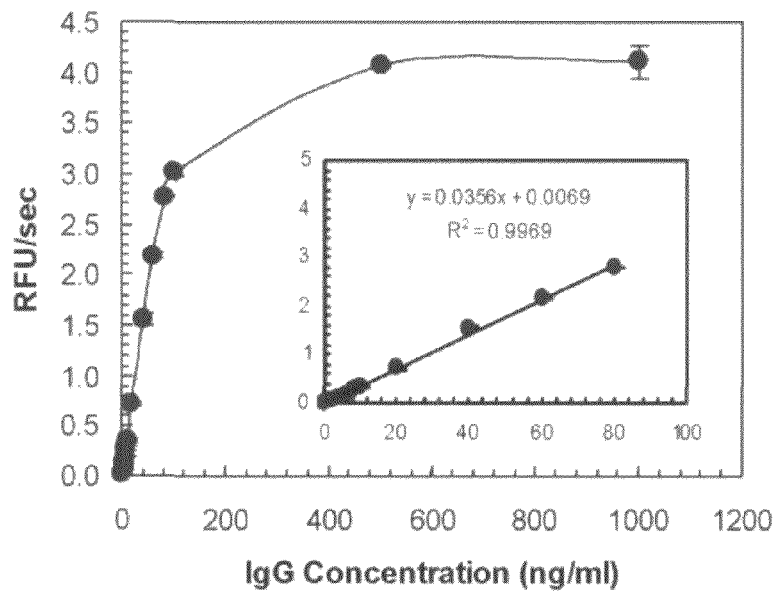
FIG. 12 is a graph of ELISA detection of IgG in a 96-well plate.
Figure 13:
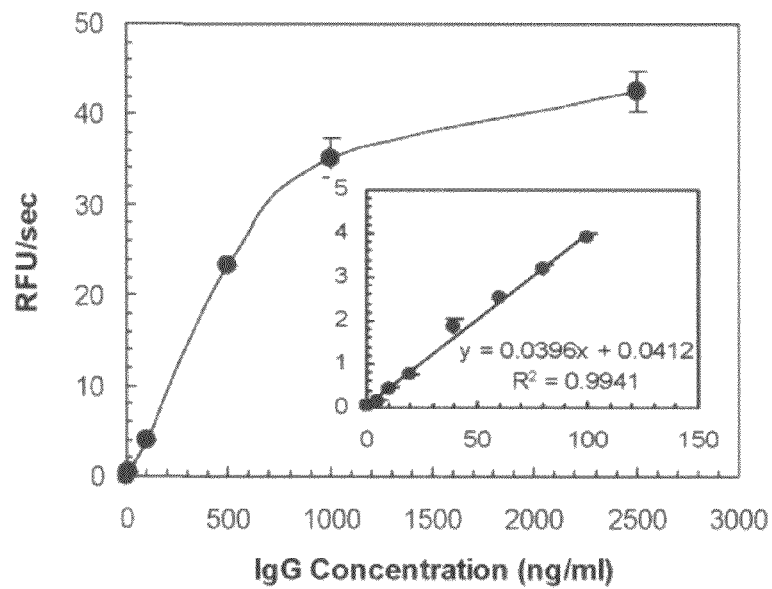
FIG. 13 is a graph of ELISA detection of IgG in a PEI-treated microchannel.

FIGS. 12 and 13 show the performance of ELISA in microchips and in 96-well plates. ELISA detection of the rat IgG was carried out over concentrations of 0 to 3 mg/L. The same concentrations of first and second antibodies were used in the study, although larger amounts (liquid volumes) were used for the 96-well plates. FIG. 12 shows the ELISA assay results on 96-well plates. A linear relationship between the fluorescence signal and the antigen concentration was observed from 2 ng/mL to 100 ng/mL. When the antigen concentration was lower than 2 ng/mL, the signal could not be distinguished from the background noise. At concentrations higher than 100 ng/mL, the fluorescence signal did not increase linearly and reached a plateau at 500 ng/mL. The results for the PEI-treated microchannel are given in FIG. 13, which shows a dynamic linear range from 5 ng/mL to 500 ng/mL.

Compared with the conventional 96-well format, the microchannel provided a wider dynamic range and a similar low detection limit even though a much smaller sample (antigen) volume was used. Due to the small dimensions of the microchannel, the diffusion time for the molecules to reach the channel surfaces, which is proportional to the square of the diffusion length, is much shorter. Therefore, the incubation times required for the protein binding and enzymatic reaction are much shorter, less than one tenth, in the microchannel than in the 96-well plate. The superior performance in the microchannel was made possible because of the surface modification with the amine-bearing polymer, PEI.

Table 1 compares the amount of reagent and incubation time needed for each ELISA in a 96-well plate versus a microchip. As can be seen, the amounts are significantly less for the microchip. For the microchip, the experimental conditions column shows the numbers used for the reported experiments and the amount required column shows the required (i.e. minimum) amounts and times for the microchip having a channel of 140 μm×125 μm.

TABLE 1

| | 96-Well Plate | | Microchip | | | |
|---|---|---|---|---|---|---|
| | | | (Experimental Conditions) | | Microchip (Amount Required) | |
| Procedure | Amount (μL) | Incubation time (min) | Amount (μL) | Incubation time (min) | Amount (μL) | Incubation time (min) |
| 1st Antibody | 100 | >120 | 1 | 60 | 0.26 | <10 |
| Blocking | 100 | >120 | 1 | 60 | 0.26 | <10 |
| IgG/sample | 100 | >120 | 1 | 60 | 0.26 | <10 |
| 2nd Antibody | 100 | >120 | 1 | 60 | 0.26 | <10 |
| Substrate | 100 | 5 | 1 | 1 | 0.26 | <1 |
| Total | 500 | >485 | 5 | 241 | 1.3 | <41 |

XPS Analysis

To determine the presence and quantify the atomic composition of nitrogen entities, three PMMA surfaces were characterized by XPS: the pristine, HMD modified, and PEI modified surfaces. The X-ray photoelectron survey spectra of all three surfaces displayed two obvious peaks centered at approximately 285 eV and 532 eV. These peaks indicated the binding energy at C 1s and O1s core levels, respectively. However, only the HMD modified and PEI modified surfaces had another peak at the binding energy around 400 eV, corresponding to the nitrogen is core level. In other words, both polymer-treated surfaces had a significantly increased nitrogen content, which was negligible or not present on the pristine PMMA surface.

The atomic compositions of the pristine, HMD modified, and PEI modified surfaces are summarized in Table 2. Total nitrogen compositions on PEI and HMD treated surfaces were 1.59% and 0.63%, respectively.

TABLE 2

| Species | | PMMA Mass conc. (%) | HMD-PMMA Mass conc. (%) | PEI-PMMA Mass conc. (%) |
|---|---|---|---|---|
| $C^{1s}$ | C | 40.07 | 41.35 | 40.17 |
| | C—O O— | 16.86 | 14.98 | 18.01 |
| | C=O | 11.37 | 12.06 | 11.4 |
| | Total C 1s | 68.3 | 68.39 | 69.58 |
| $O^{1s}$ | O | 16.07 | 14.93 | 15.75 |
| | O=C | 15.52 | 16.06 | 13.08 |
| | Total O 1s | 31.59 | 30.99 | 28.83 |
| $N^{1s}$ | Total N 1s | 0.11 | 0.63 | 1.59 |

For PEI molecules, the ratio of primary, secondary, and tertiary amine groups is 1:2:1. Only the primary and secondary amines in the PEI molecules would be able to react with glutaraldehyde to form the binding sites for the antibody. These amine groups together accounted for 1.19% total nitrogen on the PEI modified PMMA surface, which was about twice of that found on the HMD modified PMMA surface. It is noted that all nitrogen atoms in HMD are from primary amine groups.

It has been reported in *Anal Chem.* 2002, 74, 379-385, that the primary amine density on the HMD-treated PMMA surface was 0.28±0.03 nmol $NH_2/cm^2$, which was in excess of the amount required for binding all antibody molecules on the surface. The average diameter of IgG antibodies, as estimated from AFM images, is between 7 and 10 nm and a densely packed antibody layer will have the surface density of 0.00432 nmol antibody/$cm^2$. Hence, the amount of the surface active amine groups on the HMD modified PMMA surface should be sufficient for binding all first antibodies applied in this study. However, the amount of active antibody bound on the PEI modified PMMA surface was ~10 times that of the HMD modified surface, which cannot be explained by the mere two-fold difference in their active amine groups.

The difference was attributed to the differing molecular sizes of HMD and PEI. In particular, the molecular structure of PEI contributes to the beneficial spacer effect that allows the antibody to stay away from the hydrophobic polymer surface and thus avoid denaturation upon binding on the polymer surface. In contrast, the short spacer effect of HMD is insufficient to keep the large antibody molecules away from the surface and overcome steric hindrance from the vicinity of the PMMA surface.

Atomic Force Microscopy (AFM)

Figure 14:
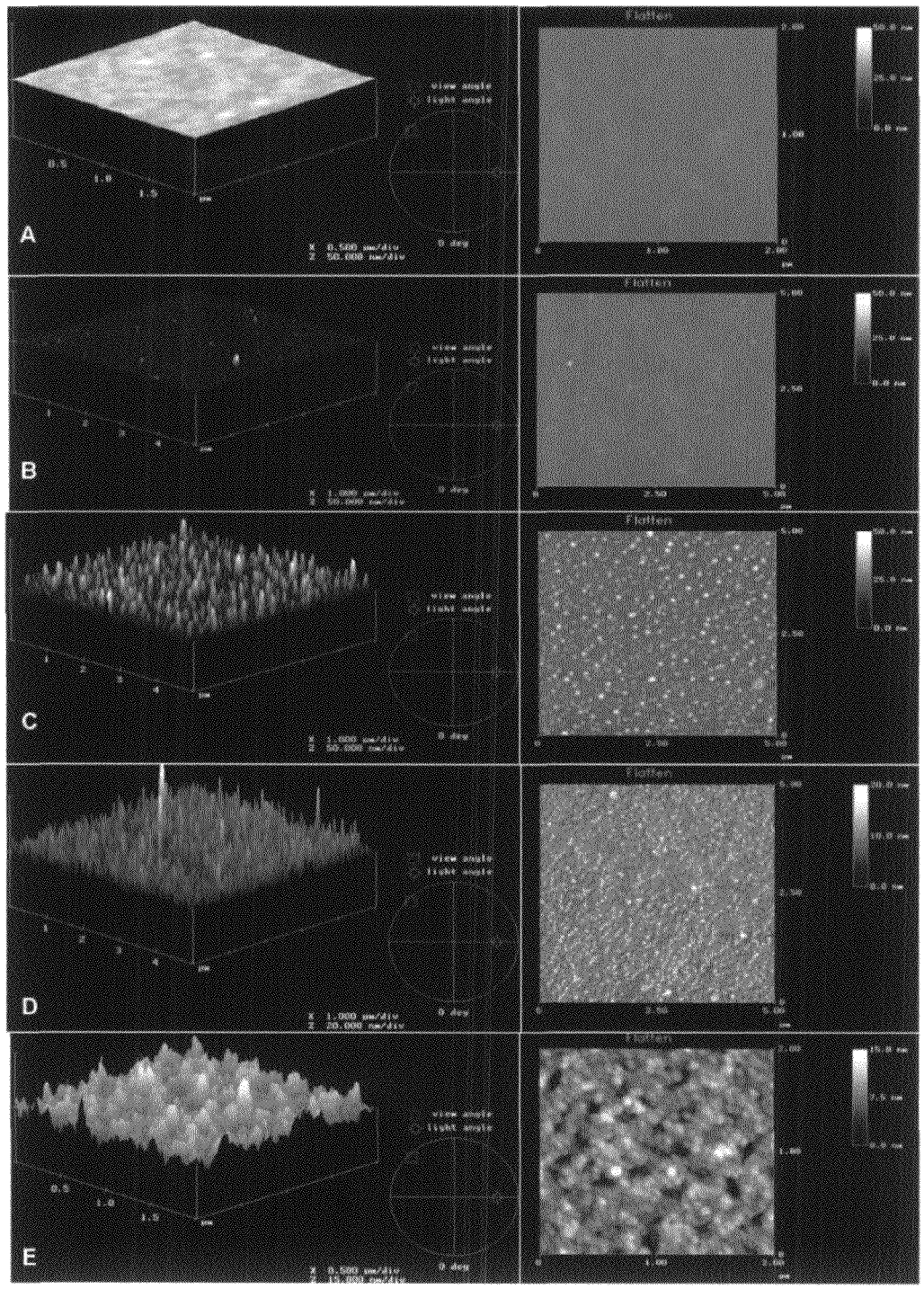
FIG. 14 shows five atomic force microscopy images of various modified surfaces.

To verify this spacer effect, atomic force microscopy (AFM) was used to investigate the morphology of the three PMMA surfaces. FIG. 14 shows the taping mode AFM images of five different immuno surfaces. The unmodified PMMA surface was prepared by spin coating PMMA/toluene solution on a clean silicon substrate. The unmodified surface (FIG. 14A) displayed a nice and flat surface with a root-mean-square (RMS) roughness value of 0.4 nm. The HMD-modified surface (FIG. 14B) displayed some small white spots and the RMS roughness value increased to 1.4 nm. For the PEI treated PMMA surface (FIG. 14C), there were many bright spots observed and their dimension ranged from several nm to more than 20 nm. The RMS roughness value increased to 3.6 nm for the PEI-treated PMMA surface. The PAH-treated surface (FIG. 14D) also showed increased RMS roughness. The difference in surface morphology between PEI and PAH can be attributed to the fact that PEI is highly branched, whereas PAH is highly linear. The images show that the polymeric PEI (and PAH) molecules on the PMMA surface were able to significantly increase the distance between the antibody and the surface, and thus afforded the antibody sufficient spatial freedom, allowing more antibodies to bind on the surface with their activities largely preserved. Consequently, the PEI-treated PMMA microchannels gave higher fluorescence signals with improved signal/noise ratio and performed better for ELISA applications. FIG. 14E shows the images of globular antibodies on the PEI treated PMMA surface, Chen et al. reported in *Langmuir* 2003, 19, 2859-2864, that the orientation of IgG antibody was better on an $NH_2$ (positively charged) surface than on a COOH (negatively charged) surface. Thus, the $NH_2$ group and positive charge on PEI molecules may also improve antibody binding efficiency, although the antibody binding is by covalent bonds and not dictated by the electrostatic effect.

Example 2

Fabrication of PMMA Microchannel

A PMMA mold for microchannels (140 μm wide, 125 μm deep, and 1.5 cm long) was fabricated as described in Example 1.

Modified PMMA Microchannels

The PMMA microchannels were aminated with PEI (MW 75,000, Sigma Chemical Co., MO) to enhance antibody binding. A partial factorial screening design based on the JMP 5.1 software (SAS Institute Inc. Cary, N.C.) was used to investigate four independent variables:

1. PEI concentration (0.2% or 1%);
2. PEI solution pH (7.0 or 11.5);
3. incubation time (20 min or 1 hour); and
4. incubation temperature (25° C. or 50° C.).

Sodium hydroxide and hydrochloride were used to adjust the pH value of the PEI solution. PMMA plates were directly immersed in the PEI solution (0.2 or 1.0%; pH 7.0 or 11.5) at a constant temperature (25 or 50° C.) for 20 or 60 min. The aminated PMMA plates were then placed in glutaraldehyde (1% w/v) at room temperature for 30 min. The PMMA surface was thoroughly rinsed with distilled water after each treatment step. Finally, the treated microchannels were air-blow dried and ready for antibody binding. The zeta potentials of treated and untreated PMMA surfaces were measured and used to evaluate the significance level of each variable analyzed with the JMP software. Unless otherwise noted, the following optimized conditions for PEI treatment were used: 0.2% PEI solution (pH 11.5) at room temperature for 1 hour. The amount of PEI on the PMMA surface was also quantified by analyzing the surface atomic nitrogen content by X-ray photoelectron spectroscopy.

Effects of PEI Surface Modification

The effects of PEI treatment on first antibody binding on the microchannel surface and subsequent ELISA performance were studied. One μL of the first antibody solution (1 or 10 mg/L) was applied to the pristine (untreated) and PEI modified PMMA microchannels. After 1 hour incubation, the microchannels were washed and air-blow dried. The actual amounts of the first antibody bound to the microchannels were determined indirectly by completing the remaining ELISA steps. The enzyme reaction rate (RFU/sec) was monitored and used as an indicator of the enzyme activity, which should be proportional to the amount of the first antibody bound on the microchannel surface when excessive amounts of antigen ($3\times10^6$ cell/mL) and second antibody (1 mg/L) were applied in the assay.

*E. coli* Adsorption/Binding Kinetics in Microchannels

The binding kinetics between the antigen (*E. coli* cell) and the first antibody on the microchannel surface was also studied. Each PEI treated and untreated microchannel was loaded with 1 μL of the first antibody solution (10 mg/L) and incubated for 1 hour, washed, air-blow dried, sealed with Scotch tape, and then blocked with the blocking solution for 1 hour. After blocking, 1 μL of the antigen solution ($3\times10^6$ cell/mL) was added into each microchannel and incubated for various time periods, followed by completing the remaining ELISA steps.

ELISA for the Detection of *E. coli* O157:H7 cells

Inactivated *E. coli* O157:H7 cells ('analyte' or antigen), Affinity Purified Antibody to *E. coli* O157:H7 (first antibody), and peroxidase-labeled Affinity Purified Antibody to *E. coli* O157:H7 (second antibody) were purchased from KPL, Inc. (Gaithersburg, Md.), reconstituted in distilled water and stored at −80° C. until use. The substrate solution was prepared by dissolving 3 g/L of 3-p-hydroxyphenylpropionic acid (HPPA) (Sigma Aldrich, St. Louis, Mo.) in Tris-HCl buffer (0.15 M, pH 8.5). Prior to use, 1 μL of 30% hydrogen peroxide was added to every 7.5 mL of HPPA solution and mixed thoroughly. The washing buffer (PBW) was prepared from Dulbecco's phosphate buffered saline (PBS, pH 7) (invitrogen Life Technologies, Carlsbad, Calif.) and contained 0.1% polyoxyethylenesorbitan monolaurate (Tween 20™) (Bio-Rad Laboratories, Hercules, Calif.) and 0.5% bovine serum albumin (BSA) (Invitrogen Corporation, Grand Island, N.Y.). The blocking buffer contained PBS, 0.1% Tween 20™, 1% BSA, and 0.05% sodium azide (Sigma Aldrich, St. Louis, Mo.). ELISA procedures were carried out in modified PMMA microchannels and Falcon multi-well plates (BD Bioscience, San Jose, Calif.) for comparison.

ELISA in Microchanneis

ELISA in microchannels was performed as in Example 1, except that the antigen was *E. coli* O157:H7 cells at concentrations ranging from zero up to $3\times10^7$ cell/mL.

Elisa in 96-Well and 384-Well Plates

To each well, 100 μL (96-well plate) or 50 μL (384-well plate) each of the following solutions were added in sequence: first antibody (10 mg/L), blocking, antigen (0–3× $10^6$ cell/mL), second antibody (1 mg/L), and substrate solutions. Between additions of the different solutions, the individual wells were washed with the PBW solution (200 μL for 96-well plate, 100 μL for 384-well plate) three times. The first antibody was incubated in the well at 4° C. overnight. The other incubation steps were done at room temperature for 3 hours or at 4° C. overnight. The reaction was detected by TECAN GENios plate reader using 320-330/410-420 nm as the excitation and emission filters, respectively.

Effects of Antibody Concentrations on ELISA Performance

The effects of the amounts of first and second antibodies on ELISA performance were studied to optimize their concentrations for *E. coli* O157:H7 detection. Various amounts of the first antibody (0, 1, 10, 100 mg/L) and the second antibody (1 mg/L, 10 mg/L) were added to PEI modified microchannels. The antigen levels tested were 0 (negative control), $3\times10^6$, and $3\times10^7$ cell/mL.

Zeta Potential Analysis

Zeta ($\zeta$) potentials of untreated and treated PMMA surfaces were measured according to the method of Walker et al. Briefly, flat PMMA plates (3 cm×5 cm×0.15 cm) were loaded against an asymmetric clamping cell (Anton Paar, Graz, Austria) attached to a streaming potential analyzer (EKA, Brookhaven Instruments, Holtsville, N.Y.). A potassium chloride solution (1 mM) was used as the background electrolyte in all experiments. For the $\zeta$ potential measurement of sample surface, the pH of KCl solution was first adjusted to ~7 and recorded during the test. After loading the test surface and preparing the background electrolyte, the entire bypass system was flushed thoroughly with 1 mM KCl solution for 10 min (5 min in each direction), followed by rinsing the measuring cell for 20 min (10 min in each direction). $\zeta$ potential was then measured four times, with alternating flow direction of the solution (2 measurements in each direction). The test sample's $\zeta$ potential, $\zeta_{Test}$, was then calculated as follows:

$$\zeta_{Test} = 2\zeta_{AVG} - \zeta_{spacer}$$

Where $\zeta_{AVG}$ is the average of four measurements of the test surface and $\zeta_{spacer}$ is the streaming potential measurement with the reference PMMA surface (untreated PMMA) at the same test pH. Detailed description of $\zeta$ potential measurement can be found in Walker et al., *Langmuir* 2002, 18, 2193-2198.

X-Ray Photoelectron Spectroscopy (XPS)

The surface elementary compositions of the PMMA plates before and after amination with PEI were analyzed with a Krotos AXIS ultra X-ray photoelectron spectrometer. Measurements were obtained using a monochromatic Al K$\alpha$ X-ray source (240 W) and charge neutralization. The samples were analyzed with a 30° take-off angle. Deconvolution of spectral peaks was performed using the Kratos software and the spectra of C(1s) (280-300 eV binding energy), O(1s) (528-542 eV binding energy), and N(1s) (392-410 eV binding energy) were recorded.

Results

PEI Surface Modification

Table 3 shows the results of the experiments investigating the four independent variables: PEI concentration, PEI solution pH, incubation time, and incubation temperature.

TABLE 3

| Run | pH | Conc. (%) | Time (min) | Temp (° C.) | Response ($\zeta$ Potential) |
|---|---|---|---|---|---|
| 1 | 7 | 0.2 | 60 | 50 | 12.16 |
| 2 | 11.5 | 0.2 | 60 | 25 | 32.95 |
| 3 | 7 | 1 | 20 | 50 | 22.34 |
| 4 | 11.5 | 1 | 60 | 50 | 42.26 |
| 5 | 7 | 1 | 60 | 25 | 1.83 |
| 6 | 7 | 0.2 | 20 | 25 | 9.1 |
| 7 | 11.5 | 1 | 60 | 50 | 35.33 |
| 8 | 11.5 | 0.2 | 20 | 25 | 39.38 |
| 9 | 11.5 | 1 | 20 | 25 | 25.72 |
| 10 | 11.5 | 1 | 20 | 25 | 28.67 |
| 11 | 7 | 1 | 20 | 50 | 7.35 |
| 12 | 7 | 1 | 60 | 25 | 9.4 |
| 13 | 7 | 0.2 | 60 | 50 | 7.12 |
| 14 | 7 | 0.2 | 20 | 25 | 6.68 |
| 15 | 11.5 | 0.2 | 20 | 50 | 32.64 |
| 16 | 11.5 | 0.2 | 20 | 50 | 37.91 |

Only the PEI solution pH, with a p-value of less than 0.0001 (lower than the significant level, $\alpha=0.05$), had a significant effect on the PEI treatment result. The Incubation temperature had a marginal effect, having a p-value of 0.072 (slightly higher than the significant level, $\alpha=0.05$).

Figure 15:
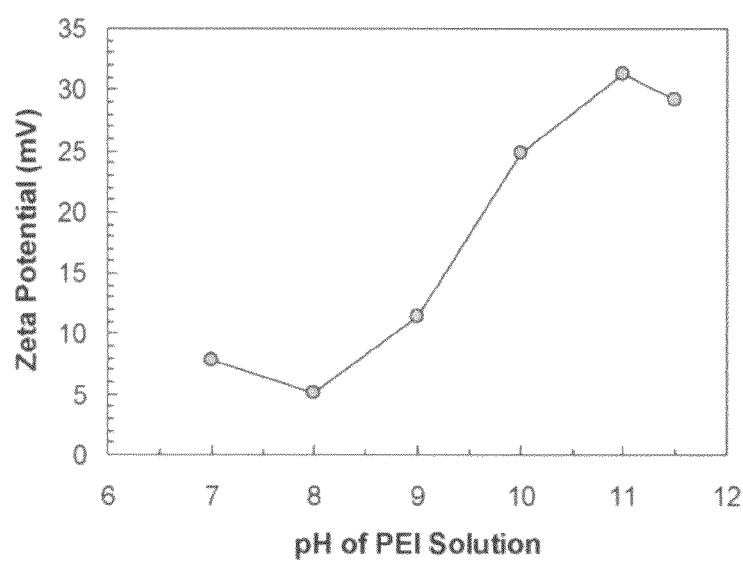
FIG. 15 is a graph of the zeta potential of PMMA surfaces treated with PEI solutions of various pH values.

Effect of pH on Zeta Potential of Treated Surface $\zeta$ potential is an important property of charged solid-liquid interfaces and provides significant insight regarding the charging behavior of solid surfaces immersed in a dielectric field. This parameter was used to investigate the amount of PEI adsorbed or attached on the PMMA surface. As shown in FIG. 15, the PEI solution pH had a significant effect on the $\zeta$ potential of the PEI-treated PMMA surface, which increased almost linearly with increasing pH from 9 to 11. This result can be attributed to the protonation property of the amine group in the solution, which is protonated as —$NH_3^+$ at pH<9 and unprotonated as —$NH_2$ at pH>11. Therefore, at pH values close to neutral, the PEI molecule is positively charged because of the amine protonation. Since the pristine PMMA surface is negatively charged with a measured $\zeta$ potential of −15 mV, the positively charged PEI molecules were directly adsorbed onto the PMMA surface through the electrostatic force at pH<9. The electrostatic effect was not strong and the adsorbed PEI molecules could be easily washed away by rinsing with water. However, at pH>9, most PEI molecules would be unprotonated and carry no charge. Thus, the PEI molecules must have attached onto the PMMA surface through covalent bonds. Covalent bonding also allowed more PEI molecules to be stably bound to the PMMA surface, as indicated by the higher values of the $\zeta$ potential for the surface treated at a higher PEI solution pH. The $\zeta$ potential was measured under neutral electrolyte condition and its value is thus an indirect measurement of the amount of PEI molecules on the PMMA surface. Thus, in some embodiments, the pH of the amine solution is from about 9 to about 11.5 or from about 9 to about 13.

XPS Analysis

To determine the presence and quantify the atomic composition of nitrogen entities, three PMMA surfaces were characterized by XPS: the pristine, PEI modified at pH 7, and PEI modified at pH 11.5. The XPS spectra of all three surfaces were compared at ~285 eV, ~400 eV, and ~532 eV representing the binding energy at C 1s, N 1s, and O1s core levels, respectively. In addition, the nitrogen peak for the pH 11.5 PEI-modified surface could be further deconvoluted into two individual peaks, one centered at 398.5 eV for the N 1s core level of amines and the other at 399.9 eV for the N 1s core level of amides. The results are shown in Table 4.

TABLE 4

| Species | Binding Energy (eV) | Plain PMMA Mass conc. (%) | PEI-PMMA at pH 7 | PEI-PMMA at pH 11.5 |
|---|---|---|---|---|
| C 1s | 284.5 | 48.28 | 49.31 | 52.64 |
|  | 286.0 | 14.06 | 14.11 | 15.41 |
|  | 288.4 | 11.20 | 10.32 | 8.02 |
|  | Total C 1s | 73.54 | 73.74 | 76.07 |
| O 1s | 531.5 | 13.04 | 12.35 | 11.2 |
|  | 533.0 | 12.65 | 12.24 | 7.18 |
|  | Total O 1s | 25.69 | 24.59 | 18.38 |
| N 1s | 398.5 | 0.78 | 1.67 | 4.24 |
|  | 399.9 | 0 | 0 | 1.31 |
|  | Total N 1s | 0.78 | 1.67 | 5.55 |

PEI treatment significantly increased the nitrogen content on the PMMA surface as a result of PEI adsorption and binding on the surface. Also, the treatment at pH 11.5 not only increased nitrogen content, but also introduced the formation of amide that was not found at the pristine and pH 7-treated PMMA surfaces. These XPS results confirmed that a substantial amount of PEI molecules were covalently bound onto the PMMA surface at pH 11.5, but not at pH 7 where the binding was mainly by electrostatic adsorption. These results were consistent with the findings from the $\zeta$ potential study. Corresponding to the increase in the nitrogen content was a decrease in the oxygen content, which was expected since PEI molecules do not contain oxygen.

Figure 16:
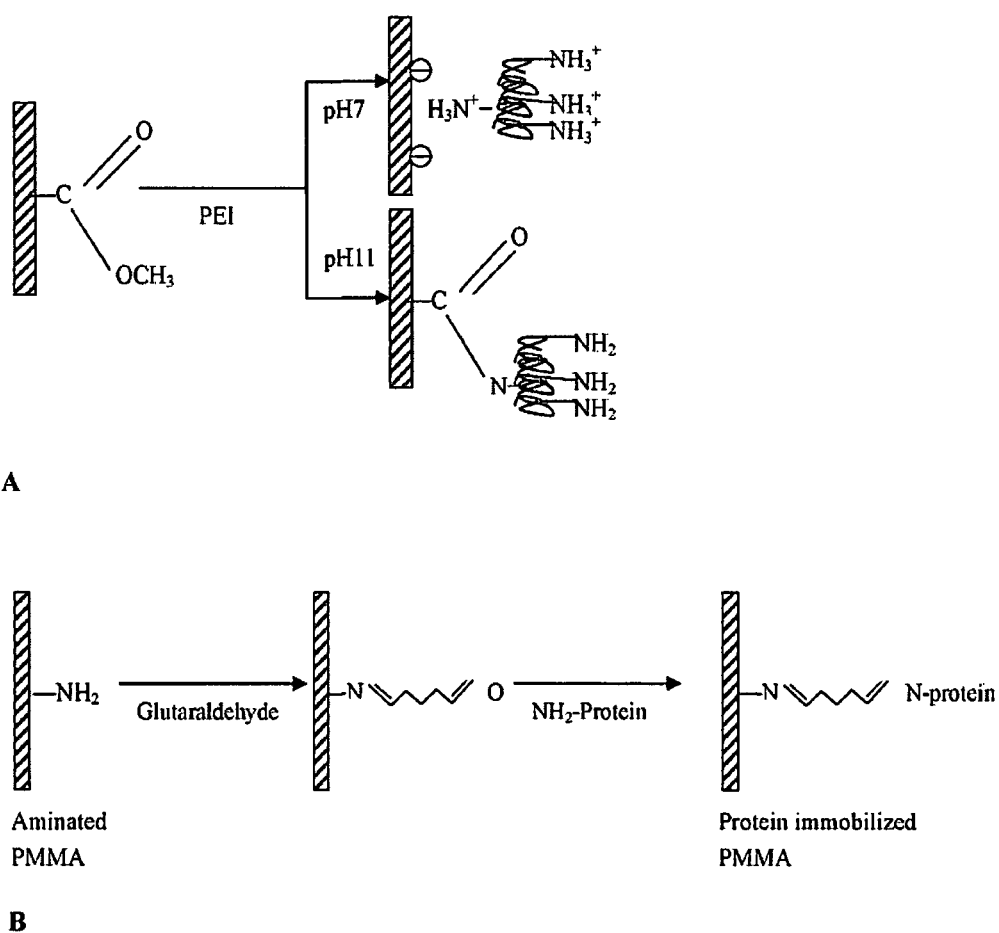
FIG. 16 illustrates two different mechanisms of PEI modification of a PMMA surface at pH 7 and pH 11; and the functionalization of the amine groups with glutaraldehyde and subsequent binding of the antibody protein molecule to the surface.

FIG. 16 illustrates the two different mechanisms of PEI modification of PMMA surface at pH 7 and pH 11. As seen in FIG. 16A, around pH 7, the PEI is attached to the PMMA substrate via the electrostatic effect, whereas at pH 11 the attachment is via covalent bonding. In FIG. 16B, the amine groups on the PMMA surface are functionalized with glutaraldehyde, whose aldehyde groups serve as the active sites for binding the antibody by forming covalent bonds with the amine group of the antibody protein molecule.

Effect of PEI Surface Modification on ELISA Performance

Figure 17:
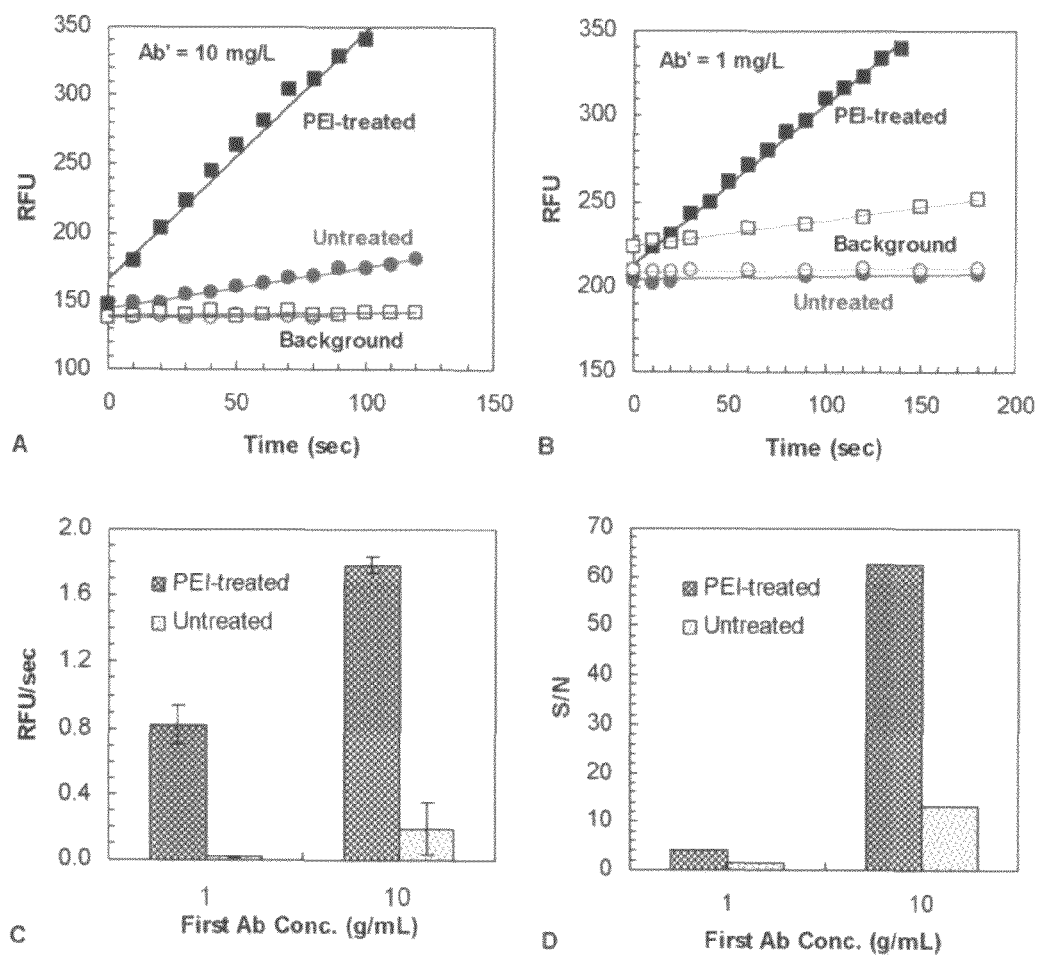
FIG. 17 is a set of graphs showing the effect of surface modification on ELISA performance for *E. coli* O157:H7 detection at different first antibody concentrations

The effects of PEI surface treatment (pH 11.5) on the microchannel ELISA performance were investigated at two different first antibody concentrations. The assay conditions were: 1 or 10 mg/L first antibody (Ab'), $3 \times 10^6$ cell/mL, and 1 mg/L second antibody. The results are shown in FIG. 17. FIGS. 17A and 17B show the time courses for ELISA carried out in PEI-treated microchannels (filled squares) and untreated microchannels (filled circles). The open squares and open circles are noise from reading the samples without adding any antigen or cells. FIG. 17C shows the reaction rates derived from slope of the data in FIGS. 17A and 17B. FIG. 17D shows the S/N ratio.

As shown, the time responses of the enzymatic reaction of HPPA as monitored by the fluorescence intensity (RFU) were much faster with stronger signals in the PEI-treated PMMA microchannels. The higher reaction rate, which was a direct result of more second antibody-enzyme conjugates present as the catalysts in the enzyme reaction, also strongly suggested that there were more active first antibodies bound on the PEI-treated PMMA microchannel surface since the amount of the second antibody-enzyme conjugate was proportional to the antigen and the first antibody present in the system.

At 1 mg/L first antibody, the background signals from the PEI-treated microchannel were also significantly higher than that from the untreated microchannel, due primarily to increased non-specific binding of the second antibody in the presence of PEI molecules on the surface. However, the background signals were reduced to a negligible level when 10 mg/L first antibody was used in the assay. Increasing the first antibody concentration also increased the fluorescence signals in the microchannel. However, this effect was more critical to the untreated PMMA surface because it had a poor antibody binding efficiency and thus would require much more first antibody in order to get detectable signals in the assay. These results suggested that the PEI treatment increased the binding efficiency of the first antibody on the PMMA surface, which in turn greatly improved the assay performance as shown in their signal strength (RFU), reaction rate (RFU/sec) or speed of detection, and the signal to noise ratio (S/N), which would determine the detection limit. Compared to the untreated surface, the PEI treatment increased the S/N ratio by 3 to 5 times depending on the first antibody concentration used in the assay.

Figure 18:
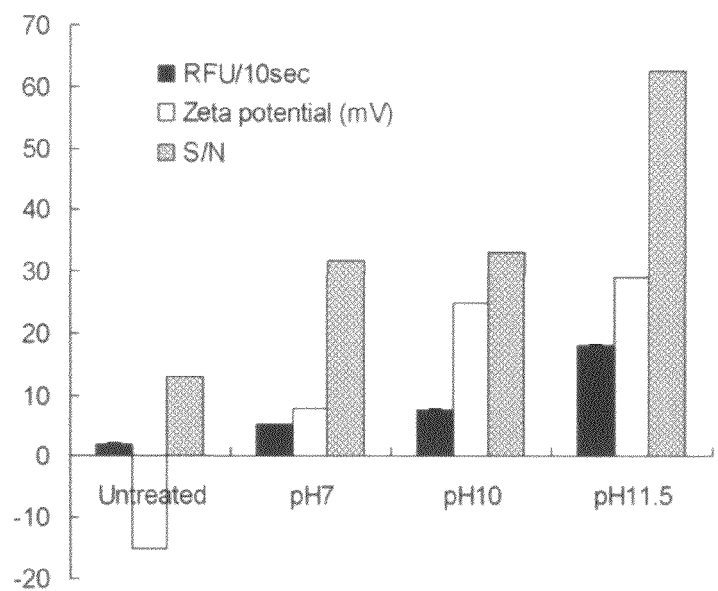
FIG. 18 is a graph showing the effect of pH on zeta potential and ELISA performance.

As discussed before, increasing the PEI treatment pH from 7 to 11.5 increased the $\zeta$ potential and PEI molecules bounded on the PMMA surface. Therefore, increasing the PEI treatment pH also should increasingly improve the ELISA performance. This was found to be the case as shown in FIG. 18. In general, increasing the pH from 7 to 11.5 also increased $\zeta$ potential and the immunoassay sensitivity (reaction rate and S/N ratio). The strong correlation between the $\zeta$ potential and the assay sensitivity provides evidence that the PEI treatment improved the ELISA performance by functionalizing the PMMA surface to facilitate the first antibody binding in the microchannel.

Effect of PEI Surface Treatment on Cell Binding Kinetics

Figure 19:
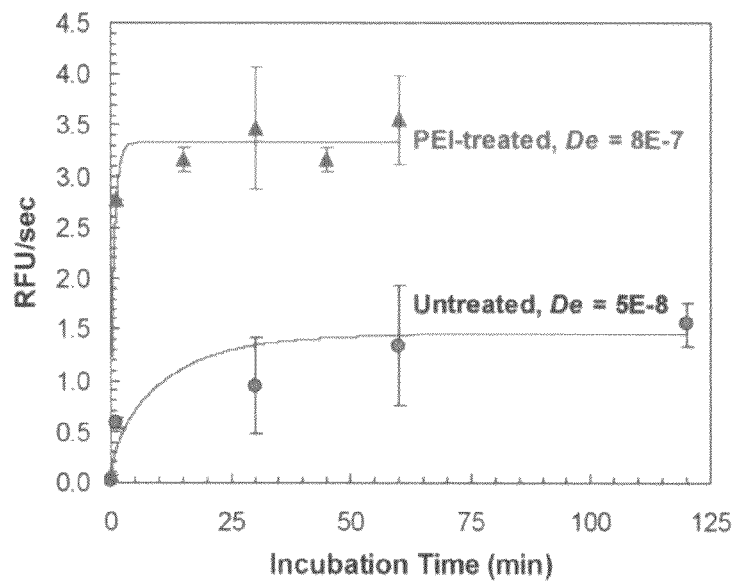
FIG. 19 is a graph showing the effect of surface treatment on the antigen *E. coli* O157:H7 cell binding kinetics.

The kinetics of *E. coli* (antigen) binding with the first antibody attached on the microchannel surface was studied. The results for both PEI-treated and untreated microchannels are shown in FIG. 19. The binding kinetics were studied by varying the incubation time, which should result in different amounts of the cells bound in the microchannel and thus the enzyme reaction rate in the assay. The reaction rate should increase with the incubation time and eventually reach a plateau when all cells (antigens) have been adsorbed onto the surface. As seen in FIG. 19, the binding was much faster in the PEI-treated microchannel, which reached the maximum reaction rate (RFU/sec) in less than 10 minutes as compared to more than 25 minutes for the untreated surface.

The experimental reaction rate data was used in conjunction with Fick's second law (Equation (1)) to estimate the effective diffusivity, D, of *E. coli* cells by fitting the data with the model predictions, which were adjusted with a proportional constant to match the plateau value shown in FIG. 19. The best D values were found to be $8 \times 10^{-7}$ cm$^2$/sec in the PEI-treated microchannel and $5 \times 10^{-8}$ cm$^2$/sec in the untreated microchannel. The much higher D in the PEI treated microchannel could be attributed to the electrostatic interaction between the positively charged PEI molecules and negatively charged cells at the reaction pH 7.4. The electrostatic attraction between the antigen and the solid surface might have dramatically increased the motion (diffusion) of the cells towards the surface, and therefore, decreased the time required for them to reach the surface. The calculated effective diffusivity was much larger than what one would have normally expected for cells with a relatively large particle size, which could become a prohibitive factor for the microchannel assay if molecular diffusion were the only mechanism for particle motion. It is clear that the PEI surface treatment has a significant effect on enhancing the cell binding (diffusion) rate, which decreases the incubation time required for binding the *E. coli* cells to the solid surface, thus facilitating their fast detection in the microchannel assay.

Effects of First and Second Antibody Concentrations on ELISA

Figure 20:
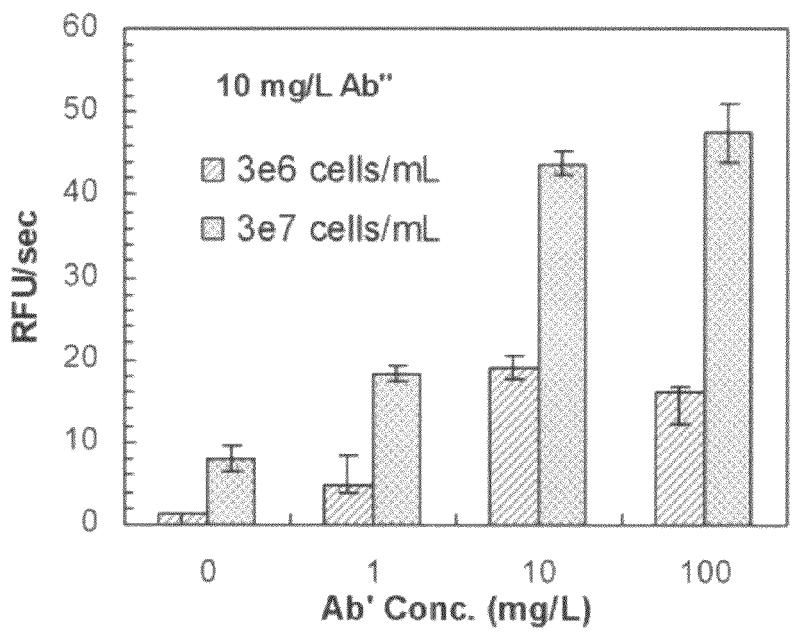
FIG. 20 is a first graph showing the effect of a higher second antibody concentration on ELISA performance.
Figure 21:
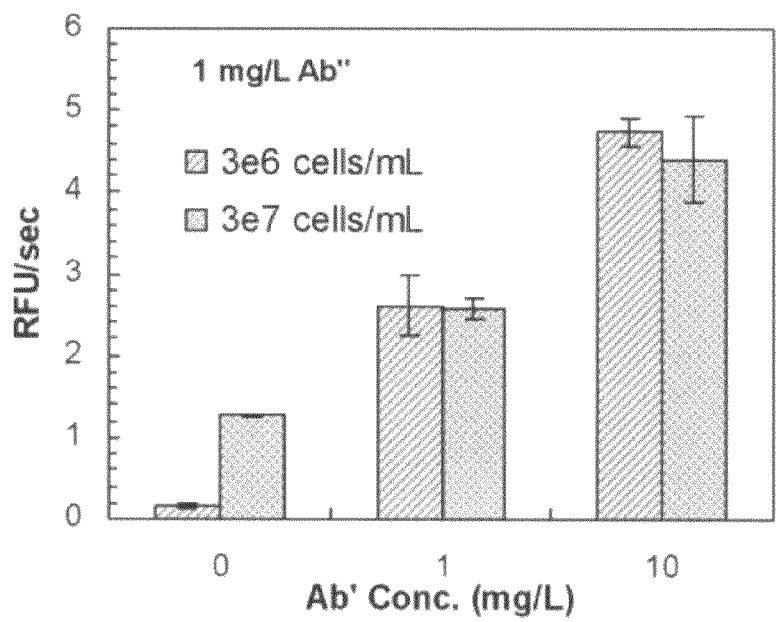
FIG. 21 is a second graph showing the effect of a lower second antibody concentration on ELISA performance.

In general, the reaction rate (RFU/sec) in the immunoassay should increase with the antigen concentration or cell numbers in the sample if there are sufficient amounts of first and second antibodies in the assay. On the other hand, insufficient or excessive amounts of the antibodies could compromise the ELISA results. The effects of first antibody (Ab') and second antibody (Ab") concentrations on the ELISA performance were thus investigated and the results are summarized in Table 5 and further illustrated in FIGS. 20 and 21. FIG. 20 used 10 mg/L of the second antibody and FIG. 21 used 1 mg/L of the second antibody.

TABLE 5

| First antibody conc. (mg/L) | 0 cell/mL Signal (RFU/sec) | 3 × 10⁶ cell/mL | | 3 × 10⁷ cell/mL | |
|---|---|---|---|---|---|
| | | (RFU/sec) | S/N ratio | (RFU/sec) | S/N ratio |
| 1 mg/L second antibody | | | | | |
| 0 | — | 0.15 | — | 1.28 | — |
| 1 | 0.15 | 2.61 | 17.4 | 2.57 | 17.1 |
| 10 | 0.02 | 4.74 | 237 | 4.41 | 221 |
| 10 mg/L second antibody | | | | | |
| 0 | — | 1.34 | — | 7.95 | — |
| 1 | — | 4.74 | — | 18.31 | — |
| 10 | 2.62 | 19.01 | 7.3 | 43.73 | 16.7 |
| 100 | 1.84 | 15.96 | 8.7 | 47.45 | 25.8 |

The reaction rate generally increased with increasing antibody concentrations to 10 mg/L. Further increasing the first antibody concentration to 100 mg/L did not show any significant increase in the reaction rate, indicating that 10 mg/L of the first antibody would be sufficient for the detection and quantification of $E. coli$ O157:H7 up to $3 \times 10^7$ cell/mL in the sample, which also required 10 mg/L of the second antibody. However, increasing the second antibody concentration also increased the background signal from the blank sample (without $E. coli$ cells) because of its nonspecific binding to the solid surface. Lowering the second antibody concentration to 1 mg/L did not discriminate the samples with $3 \times 10^6$ cells/mL from the samples with $3 \times 10^7$ cells/mL (see FIG. 21), but was still sufficient to detect the $E. coli$ cells present in these samples as compared to the blank sample (see Table 5). Also, increasing the first antibody concentration decreased the background signal and significantly improved the S/N ratio, which would be beneficial to the detection of low-level $E. coli$ samples. In general, a low background signal (noise) is required in order to achieve a low detection limit, which is desirable for the purpose of detecting the presence of $E. coli$ O157:H7 in a test sample. A combination of 10 mg/L of the first antibody and 1 mg/L of the second antibody is suggested by the results.

Figure 22:
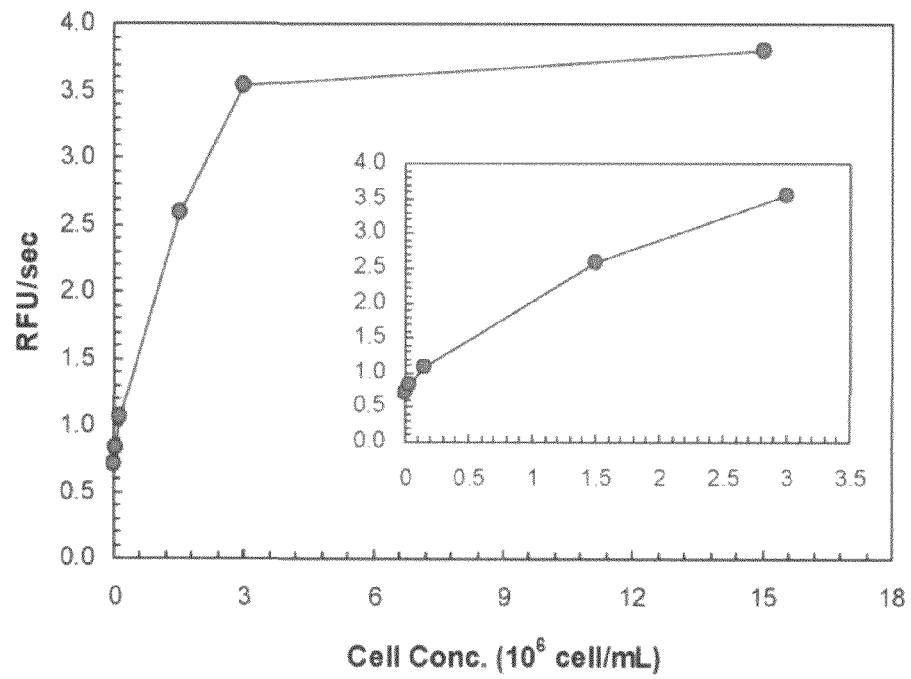
FIG. 22 is a graph showing the effect of *E. coli* O157:H7 cell concentration on ELISA performance in a PEI-treated microchannel.
Figure 23:
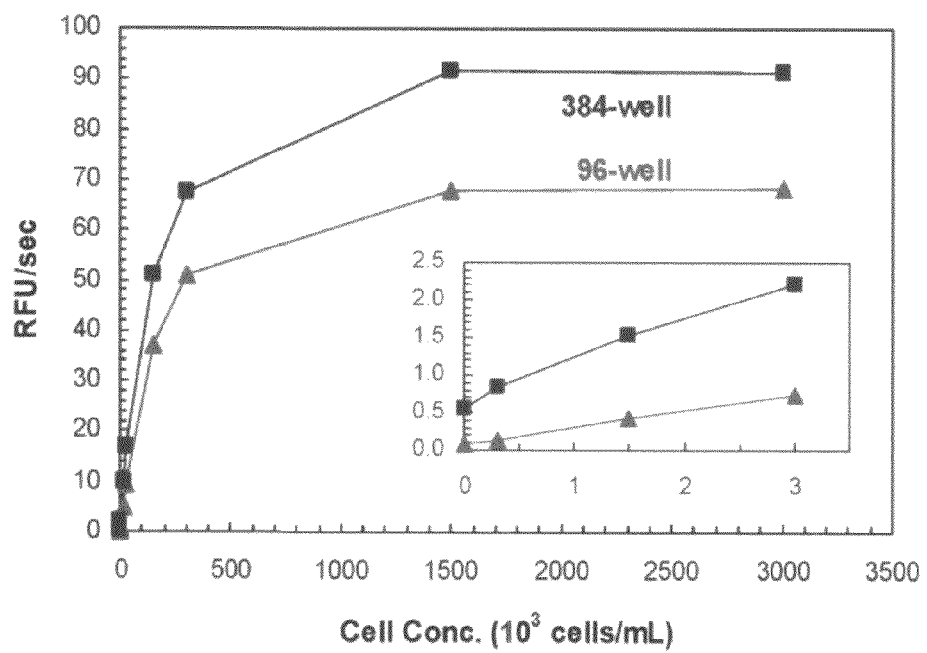
FIG. 23 is a graph showing the effect of *E. coli* O157:H7 cell concentration on ELISA performance in untreated 96-well and 384-well plates.

Comparison of ELISA Performance in 96-Well Plates, 384-Well Plates, and Microchannel A comparison of ELISA detection as affected by the cell concentration was carried out in PEI (pH 11.5)-treated microchannels and untreated multi-well plates. 10 mg/L first antibody and 1 mg/L second antibody were used. The results for the microchannels are shown in FIG. 22 and the multi-well plates are shown in FIG. 23. In general, the assay carried out in the microchannels worked well with a linear detection range up to $3 \times 10^6$ cells/mL. The linear detection range was limited by the amount (1 mg/L) of the second antibody used in the assay, as discussed above.

Compared to the conventional multi-well ELISA, the microchannel ELISA requires a higher concentration level ($10^5$ cells/mL) in the sample because of its much smaller volume (~0.25 µL), which is two to three order of magnitude smaller than the multi-well plates (50 to 100 µL). The total number of cells present in the 1.5-cm long microchannel (0.25 µL) was only 25 cells and the actual number of cells present in the detection region (less than 3 mm long) was only 5 cells when the sample concentration was $10^5$ cells/mL.

Figure 24:
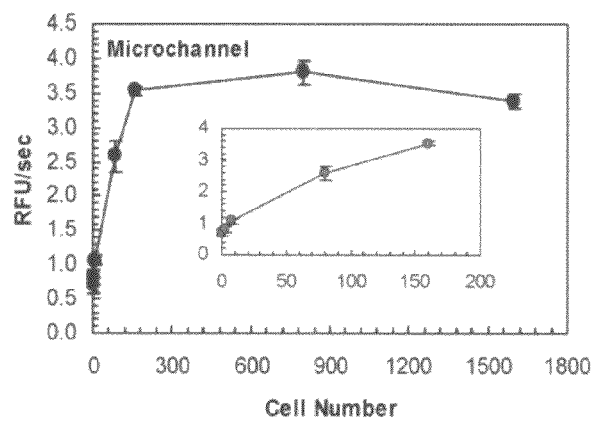
FIG. 24 is a comparison of the detection level versus the total number of cells in PEI-treated microchannels.
Figure 25:
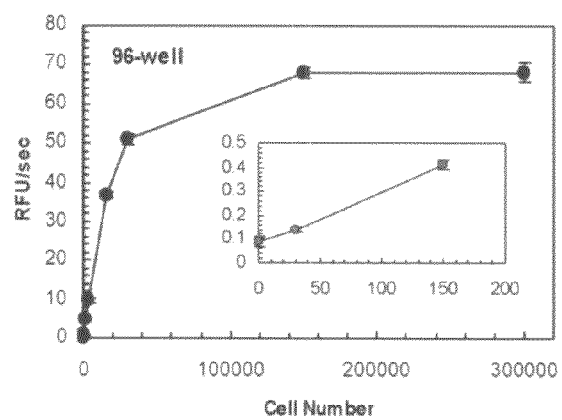
FIG. 25 is a comparison of the detection level versus the total number of cells in untreated 96-well plates.
Figure 26:
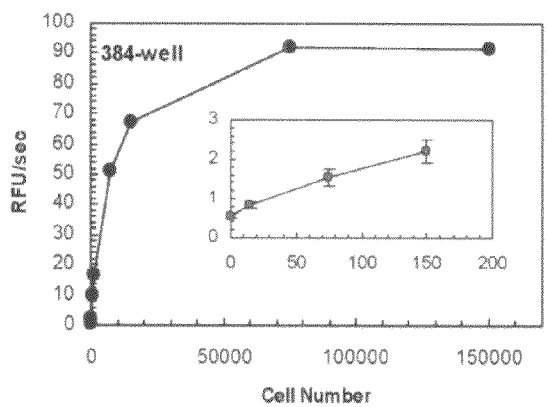
FIG. 26 is a comparison of the detection level versus the total number of cells in untreated 384-well plates.

FIGS. 24-26 show the reaction rate as a function of the total cell number in a microchannel, 96-well plate, and 384-well plate, respectively. The total number of cells required for detection in the microchannel is close to or less than in the multi-well plates, even though the microchannel has a much shorter light path length (0.125 mm) for detection than those for the multi-well plates (3.3 mm for 96-well and 3.85 mm for 384-well plates). As low as 5 to 8 cells can be detected in the microchannel, whereas 15 to 30 cells would be required for detection in the conventional 384-well and 96-well plates. Thus, the PEI-modified microchannel ELISA has a high sensitivity for the detection of $E. coli$ O157:H7. Further improvement in the detection limit (to single cell) can be achieved by increasing the depth of the microchannel.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A method for aminating the surface of a polymeric substrate, comprising:
    providing a polymeric substrate having a surface; and
    contacting the surface with an amine solution comprising an amine-bearing polymer, the polymer having a reactive nitrogen atom in either the backbone or a pendant group, to obtain the substrate with an aminated surface;
    wherein the amine solution has a pH of from about 9 to about 13.

2. The method of claim 1, wherein the amine solution comprises from about 0.1% to about 10% (w/v) of the polymer.

3. The method of claim 1, wherein the contacting step occurs at a temperature of from about 20° C. to about 100° C.

4. The method of claim 1, wherein the contacting step occurs for a period of from about 5 minutes to 12 hours.

5. A method for aminating the surface of a polymeric substrate, comprising:
    providing a polymeric substrate having a surface;
    contacting the surface with an amine solution comprising an amine-bearing polymer, the polymer having a reactive nitrogen atom in either the backbone or a pendant group, to obtain the substrate with an aminated surface; and
    treating the surface of the substrate with a basic aqueous solution prior to contacting the surface with the amine solution;
    wherein the amine solution has a pH of from about 9 to about 13.

6. The method of claim 5, wherein the basic solution comprises from about 0.1 N to about 6 N of NaOH.

7. The method of claim 5, wherein the basic solution has a pH of from about 8 to about 14.

8. The method of claim 5, wherein the treating step occurs at a temperature of from about 20° C. to about 100° C.

9. The method of claim 5, wherein the treating step occurs for a period of from about 5 minutes to 12 hours.

10. A method for aminating the surface of a polymeric substrate, comprising: the step of
    providing a polymeric substrate having a surface;
    contacting the surface with an amine solution comprising an amine-bearing polymer, the polymer having a reactive nitrogen atom in either the backbone or a pendant group, to obtain the substrate with an aminated surface; and
    functionalizing the surface with a crosslinker solution comprising an aldehyde molecule having multiple functional aldehyde groups;
    wherein the amine solution has a pH of from about 9 to about 13.

11. The method of claim 10, wherein the crosslinker solution comprises from about 0.1% to about 10% (w/v) of the aldehyde molecule and the aldehyde molecule is glutaraldehyde.

12. The method of claim 10, wherein the functionalizing step occurs at a temperature of from about 20° C. to about 100° C.

13. The method of claim 10, wherein the functionalizing step occurs for a period of from about 5 minutes to 12 hours.

14. The method of claim 1, wherein the polymeric substrate is of a polymer selected from the group consisting of poly (methyl methacrylate) (PMMA), polyester, polyethylene terephthalate, polyurethane, ester-containing polymers, polystyrene, polycarbonate, polyethylene, and polypropylene.

15. The method of claim 1, wherein the amine solution has a pH of about 11.

16. The method of claim 1, wherein the amine solution has a pH of from about 11 to about 13.

17. The method of claim 1, wherein the amine solution has a pH from about 11.5 to about 13.

18. The method of claim 5, wherein the basic solution has a pH of from about 10 to about 14.

\* \* \* \* \*